US010709152B2

(12) United States Patent
Jin et al.

(10) Patent No.: US 10,709,152 B2
(45) Date of Patent: Jul. 14, 2020

(54) CHLAMYDOMONAS MUTANTS PRODUCED USING RGEN RNP AND METHOD FOR PREPARING PIGMENT USING THE SAME

(71) Applicant: Industry-University Cooperation Foundation Hanyang University, Seoul (KR)

(72) Inventors: Eon Seon Jin, Seoul (KR); Sang Su Bae, Seoul (KR); Kwang Ryul Baek, Goyang-si (KR); Duk Hyoung Kim, Incheon (KR); Joo Yeon Jeong, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 66 days.

(21) Appl. No.: 16/050,012

(22) Filed: Jul. 31, 2018

(65) Prior Publication Data

US 2019/0045812 A1 Feb. 14, 2019

Related U.S. Application Data

(63) Continuation-in-part of application No. PCT/KR2017/004268, filed on Apr. 21, 2017.

(30) Foreign Application Priority Data

Apr. 22, 2016 (KR) ........................ 10-2016-0049439
Mar. 31, 2017 (KR) ........................ 10-2017-0041761
Mar. 31, 2017 (KR) ........................ 10-2017-0041762

(51) Int. Cl.

| | |
|---|---|
| *A61K 9/00* | (2006.01) |
| *C12P 23/00* | (2006.01) |
| *A23K 20/179* | (2016.01) |
| *A23L 29/00* | (2016.01) |
| *C12R 1/89* | (2006.01) |
| *A23K 10/16* | (2016.01) |
| *C12N 1/12* | (2006.01) |
| *C12N 9/02* | (2006.01) |
| *A61K 9/20* | (2006.01) |
| *A23K 20/174* | (2016.01) |
| *A23L 33/135* | (2016.01) |

(52) U.S. Cl.

CPC ............ *A23K 20/179* (2016.05); *A23K 10/16* (2016.05); *A23K 20/174* (2016.05); *A23L 29/065* (2016.08); *A23L 33/135* (2016.08); *A61K 9/0053* (2013.01); *A61K 9/2018* (2013.01); *C12N 1/12* (2013.01); *C12N 9/0073* (2013.01); *C12N 9/0077* (2013.01); *C12P 23/00* (2013.01); *C12R 1/89* (2013.01); *C12Y 114/1309* (2013.01); *C12Y 114/15* (2013.01)

(58) Field of Classification Search

None
See application file for complete search history.

(56) References Cited

FOREIGN PATENT DOCUMENTS

| | | | |
|---|---|---|---|
| KR | 10-2014-0083998 | A | 7/2014 |
| KR | 10-1563148 | B1 | 10/2015 |
| WO | 2013/032412 | A1 | 3/2013 |
| WO | 2015/086795 | A1 | 6/2015 |

OTHER PUBLICATIONS

Inmaculada Couso et al., "Efficient Heterologous Transformation of Chlamydomonas reinhardtii npq2 Mutant with the Zeaxanthin Epoxidase Gene Isolated and Characterized from Chlorella zofingiensis", Mar. Drugs, 2012, pp. 1955-1976, vol. 10; doi:10.3390/md10091955.
Wenzhi Jiang et al., "Successful Transient Expression of Cas9 and Single Guide RNA Genes in Chlamydomonas reinhardtii", Eukaryotic Cell, Nov. 2014, pp. 1465-1469, vol. 13, No. 11.
Robert E. Jinkerson et al., "Molecular techniques to interrogate and edit the Chlamydomonas nuclear genome", The Plant Journal, 2015, pp. 393-412, vol. 82, doi: 10.1111/tpj.12801.
Sojung Kim et al., "Highly efficient RNA-guided genome editing in human cells via delivery of purified Cas9 ribonucleoproteins", Genome Research, 2014, pp. 1012-1019, vol. 24, Published by Cold Spring Harbor Laboratory Press; ISSN 1088-9051/14; www.genome.org.
Kwangryul Baek et al., "DNA-free two-gene knockout in Chlamydomonas reinhardtii via CRISPR-Cas9 ribonucleoproteins", Scientific Reports, 2017, pp. 1-7, vol. 6, No. 30620, DOI: 10.1038/srep30620.
International Search Report of PCT/KR2017/004268 dated Jul. 25, 2017 [PCT/ISA/210].

*Primary Examiner* — Padmavathi Baskar
(74) *Attorney, Agent, or Firm* — Sughrue Mion, PLLC

(57) ABSTRACT

The present invention relates to a new alga having an improved ability to produce a pigment, and when a mutant of the present invention is used, a carotenoid-based pigment, specifically, a xanthophyll can be produced by consuming less energy, so that it is possible to efficiently produce the pigment at the industrial level. Further, the pigment can be applied as a raw material for a food, a health functional food and a medicine, which include the pigment. In particular, since a DNA fragment is not likely to be inserted into a target base sequence or a base sequence other than the target, it is expected that the procedure of constructing the mutant is not regulated as a GMO, so that it is expected that the procedure of constructing the mutant can create a big economic effect in terms of an industry which produces lutein and zeaxanthin by using microalgae.

4 Claims, 14 Drawing Sheets
(5 of 14 Drawing Sheet(s) Filed in Color)
Specification includes a Sequence Listing.

【Figure 1】
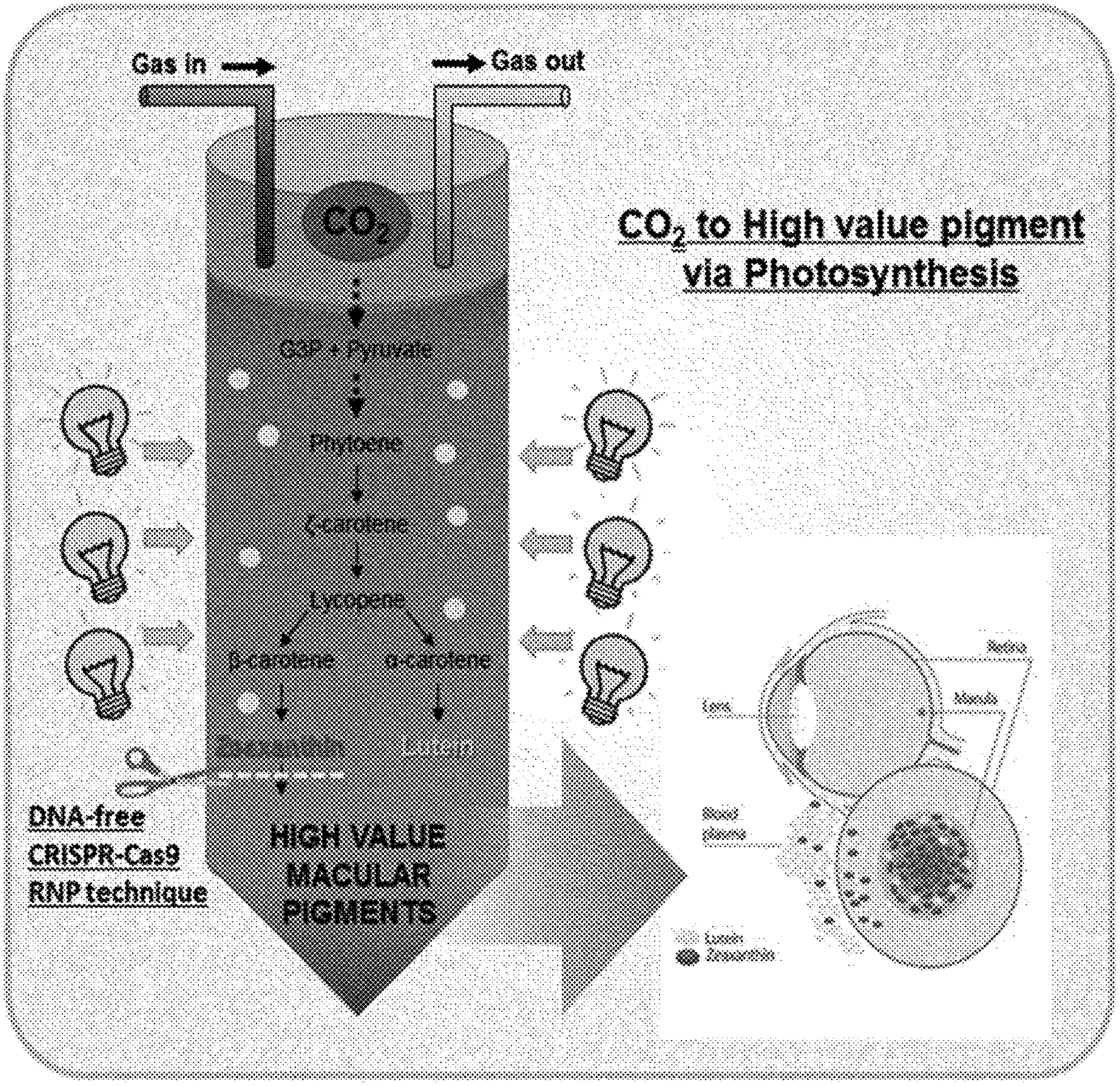

[Figure 2]

Information on zeaxanthin epoxidase (ZEP) gene of Chlamydomonas wild-type and ZEP genes in ZEP mutants 1, 2, and 3

5' UTR / CDS / 3' UTR

Target sequence

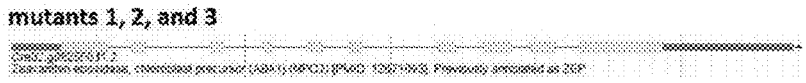

>Wild type ZEP gDNA sequence

[illegible]
GTGCGTTCGCCGGAACACCAACGCGCTTGTTTTTGCTGTGCCGCGACCATGAACTAGGCCTTATCTTGAGGTGTTAGCATG
TTTAGCCAGCGTTGGATCTGTGTGGCGAGGTTGGGGTGAGAACCCTTCCTGTGTACCTGCTCGGGCGTACCTTGTGCCCCACCGCTGACTGGCTTACTTA
ATGACAAAACGCAG[illegible]
GTGAGTAGGCAATCCAGCTGTGCATCCAGTCGCGCGGTTGCGGAGGTCGTCTCGGGAAACG
CGACGTGGCGTCCACTCGCCCAAGGAGTGGTCTCCCGCAGCGTGGTCTCCCGCAGCTCGGGTGCAACACCCTGCCCCCTGCCGCGAGCGCGCTGCGCTTG
CTTATGTTGCGCAGCGGTGTGAGTTACAACAGCTTCTGTTGAAGAGCTGTCATACGAAGCACGGCGCGCTGTGGCGCTGCAGCCGTGCTGTGGAAACTCC
AACACCTCCACCGCCAGCCTGCGCACGCACACGCAATACACTCGCCTCGTGTGCCCCCTCCTCACACAACGGCATGTGACACTCAGTTTTAACTCTTATT
TTGACAGCTGAGAGCTACACGCTTGGGTGAATGGGGAGGTCCTTGATGTTTCGTTGCACTCCGTGGCTCCGGAGTCCGTGCGGACCGTCACCCACAAATG
GGAGCGCACGGCTTTCTTGTGCTGTCTGCCCCGTTAGCCACTAACTGCGAATGACCTTGACAGTTTACTTTGCTATTTTTCCTTCCAG[illegible]
GTGA
GCCGTGCGCGCGGTGTGATGGCTTTAGCGTCAGTGCTAGCATGGGGGTTGGTGGGTGGTAATCGCGGCGCCCATGGCCGGGTAGCAGCGGCCGAAAGCTG
GCGCAGAGCGCGCGTTGGACAAGCGGTCCTGTTGCCGGTATGGGCACGAGCAGGGCGCTGGTGCGGGCAAAGGGCAGAGTGGAGTTGCAGAGCAGCGCTG
GCGTCGGCTGTGCGCTCTCCAAATGGCCTCGTGGCATTCTGACGGGACACATCCTGGAAAATAGTAGCGCACCCAACTGCTGGTGGCTCCTCGTACAATC
CCCCCAATTTACAATCGCTCGTTCTGGCTCGCAG[illegible]
GTGAGAGCGTGCTAAGAAGAGCATGCACGTGGAGCGTGTAAAATTGTGTGGCCTGAAGCGGCAGTGCCTGCGGCATGGACT
AGGTGGTTGCAGCATGCTGCGCGCGTGGGTTGCCGGTCAGGAAACCGCCGGACCGAGCCGCGCAGATTCAGTCAGGAGCGGATTAGGAAGTTTGAAAAAC
AGGGTTCGGAGTGTGCAAGCGGGCTCAGGAGCTGTGGTGCCTTTCTACACCGGTCGCCCTACCAGGCACCCACTGAAACTGTAAAACCGTTGCTGCGCCG
GCGATGCCCTCTACTTCACTAG[illegible]
GTGAGATTATTGACCTTCAAGTTGGAAGGAGGGAGCGGGGGG
AGCGGAATGGAAGGAAGCAGCGTGGACGGGGCGCACGGAGGGGAGGGGACTGCGGGTCATAGCGCCGCCTTGCGGGGCGTGAGGAGTGTTGGGCGGATAT
TCAGTTTTCTTTGCCCAAGATCTTCCCACAATCCGCGTGTGTCTGACGCGGGATGTGGCCCCTGCTGCCATGGCTTCGCAG[illegible]
GTGAGCGGCG
GCGGGCGGGCGAGCGAGGGCTGCGGGGTCTGGAGGGTGTGTACCGGGCGGAAGGGAGGGGAAGGGAGGGGAAGGGAAGGCAGGATGCAGGCGAGGGCAGG
ATGTGATGGTGGGAAGAGGGCGTGGCGAGCAGCAACTGGAAAGGTGGTGGGTAAAAAAATGGTCCATGAATATGGCTCGGTACAGTTCAAAGCATGGAAA
TGGAACCCGCCGTCTGCTGCACCATGGGCGTGAGCGGGGAGTACGCGACTCCTGGACAGCCGTAACAATGCGGATGGCCTCAACAAGCCAGGAGCGGCAC
GAACCCAGCTCACGAGCGCACAGCGTGCCAGGACGGCGGCCGGCAAGGATGAAATGTTTTTCCTAATATAAATGCGGACTCCTGACGCATTATATCCATT
TTGCCACTGAGCCAAAGACACATATATACACGTGCGCCGCCGTCCTGCGCCACAGCCGCCTAGCGCTCCGGCCGCGCCCGGTTCCCTCGGCGTCATGCGC
TGGAGCCCCCTCGCACCCTGCACCGCAAAGCCCATCAACACCACACTCGTCCCCACACCGCGAGTCACCGCCACTGCACTCGCTGTCCCTCAACCCGTCA
CAATCTCGCCGACACGCGATAACGAACCCACGCAG[illegible]
GTACGGAAA
AAGGGAGAGCGGGGTGGCTGGAGGGCGGGAAAGGGCGAAGGGGCGGAGAAAGAAATGACTAGGGGATGGTGTTCATTTGTGGGATTGAGAGGGGTCCGCG
GATCCCGGCAGAGGGCGCCAGTGGCAAGGCGTGGGAGTCGCGGGGCGGACAATGCTGGGCCAGGGGCGCCTAGTCACCCCGGGACACTGTCTCAGTATGC
CGCCGTCCCGGCCGCGCCGCACAG[illegible]
GTGAGAGCTGCAACCAGCGTAGTCGGGCTGG
GCTGCTGTGGGCAGGGTCGGGTTGGGTTGGGCGCACGTGGGCGGCGAGTGTATGTGCAGTGTGACGTGCACACTATCATAATACTTTATGCTCACCGCAC
CGCGCCGCGCCGCACCACGCGCCACAG[illegible]
GTGAGCGGCTGCCGGGCTGGGGGGGGTGGAGGGAGAGGAGGAGGATTGCGGGGA
GACGAGGGAGGGCAAGGCAGGCGCTGCCTTCGTGGATGCACCGCCCCGTCGTTAGCAGGACCTCAGGAACTCGTCCCCAAAACCACAACAGAACCCCCAA
TATCGCCTCTTCCTTCACTGCTTGTCACGCCTGGTCCGCCGACCGCAG[illegible]

【Figure 3】

| | #RGEN Target (5' to 3') | Position | Cleavage Position | Direction | GC Contents (w/o PAM) | Out-of-frame Score | Mismatch 0 | Mismatch 1 | Mismatch 2 |
|---|---|---|---|---|---|---|---|---|---|
| RGEN1 | CACCAGCTGCGGGACCGAGCTGG | 638 | 9.732573433 | - | 75 | 84.3 | 1 | 0 | 0 |
| RGEN2 | GCCGTTGCACTTCTGAAGCAGGG | 724 | 13.98509426 | + | 55 | 75.3 | 1 | 0 | 0 |
| RGEN3 | TCCGGCGAACGCACCTGGATGGG | 811 | 17.31696624 | - | 65 | 75.4 | 1 | 0 | 0 |
| RGEN4 | TGGTGGGCGCCGACGGCATCTGG | 2569 | 33.97632617 | + | 75 | 88.2 | 1 | 0 | 0 |
| RGEN5 | CCATGGCTTCGCAGGCATCTCGG | 2868 | 37.26435774 | + | 60 | 71.2 | 1 | 0 | 0 |

【Figure 4】 a

| | total | mut | freq(%) | total | mut | freq(%) |
|---|---|---|---|---|---|---|
| RGEN1 | 4276 | 4 | 0.094 | 9541 | 0 | 0 |
| RGEN2 | 16734 | 6 | 0.036 | 19060 | 0 | 0 |
| RGEN3 | 16888 | 77 | 0.456 | 30992 | 0 | 0 |
| RGEN4 | 20274 | 9 | 0.044 | 17138 | 0 | 0 |
| RGEN5 | 15398 | 17 | 0.11 | 7867 | 0 | 0 |

b

Control

GCCATCCGCGGCGAGGGCAAGTACCGTGGACCCATC------CAGGTGCGTTCGCCGGAACACCAACGCGCTTGTTTTTGCTGTGCCGC

ZEP-RGEN3

GCCATCCGCGGCGAGGGCAAGTACCGTGGACCCATCtc----CAGGTGCGTTCGCCGGAACACCAACGCGCTTGTTTTTGCTGTGCCGC 2 ins GCCATCCGCGGCGAGGGCAAGTACCGTGGACCCAT-------CAGGTGCGTTCGCCGGAACACCAACGCGCTTGTTTTTGCTGTGCCGC 1 del GCCATCCGCGGCGAGGGCAAGTACCGTGGACCCA----------GGTGCGTTCGCCGGAACACCAACGCGCTTGTTTTTGCTGTGCCGC 4 del GCCATCCGCGGCGAGGGCAAGTACCGTGGACCCATCaacatcCAGGTGCGTTCGCCGGAACACCAACGCGCTTGTTTTTGCTGTGCCGC 6 ins GCCATCCGCGGCGAGGGCAAGTACCGTGGACCCATCt-----CAGGTGCGTTCGCCGGAACACCAACGCGCTTGTTTTTGCTGTGCCGC 1 ins

[Figure 5]

SpCas9 서열

MGSSHHHHHHVYPYDVPDYAELP[redacted]GIRIPGEKPDKKYSIGLDIGTNSVGWAVITDEYKVPSKK
FKVLGNTDRHSIKKNLIGALLFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLPGEKKNGLFGNLIA
LSLGLTPNFKSNFDLAEDAKLQLSKDTYDDDLDNLLAQIGDQYADLFLAAKNLSDAILLSDILRVNTEIT
KAPLSASMIKRYDEHHQDLTLLKALVRQQLPEKYKEIFFDQSKNGYAGYIDGGASQEEFYKFIKPILEKM
DGTEELLVKLNREDLLRKQRTFDNGSIPHQIHLGELHAILRRQEDFYPFLKDNREKIEKILTFRIPYYVGPL
ARGNSRFAWMTRKSEETITPWNFEEVVDKGASAQSFIERMTNFDKNLPNEKVLPKHSLLYEYFTVYNE
LTKVKYVTEGMRKPAFLSGEQKKAIVDLLFKTNRKVTVKQLKEDYFKKIECFDSVEISGVEDRFNASLG
TYHDLLKIIKDKDFLDNEENEDILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQKAQVSGQGDSLHEHIANLAGSPAI
KKGILQTVKVVDELVKVMGRHKPENIVIEMARENQTTQKGQKNSRERMKRIEEGIKELGSQILKEHPVE
NTQLQNEKLYLYYLQNGRDMYVDQELDINRLSDYDVDHIVPQSFLKDDSIDNKVLTRSDKNRGKSDNVP
SEEVVKKMKNYWRQLLNAKLITQRKFDNLTKAERGGLSELDKAGFIKRQLVETRQITKHVAQILDSRMN
TKYDENDKLIREVKVITLKSKLVSDFRKDFQFYKVREINNYHHAHDAYLNAVVGTALIKKYPKLESEFVY
GDYKVYDVRKMIAKSEQEIGKATAKYFFYSNIMNFFKTEITLANGEIRKRPLIETNGETGEIVWDKGRDF
ATVRKVLSMPQVNIVKKTEVQTGGFSKESILPKRNSDKLIARKKDWDPKKYGGFDSPTVAYSVLVVAK
VEKGKSKKLKSVKELLGITIMERSSFEKNPIDFLEAKGYKEVKKDLIIKLPKYSLFELENGRKRMLASAGE
LQKGNELALPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSITGLYETRI
DLSQLGGD 6xHis
HA tag
[redacted]
SpCas9

【Figure 6】
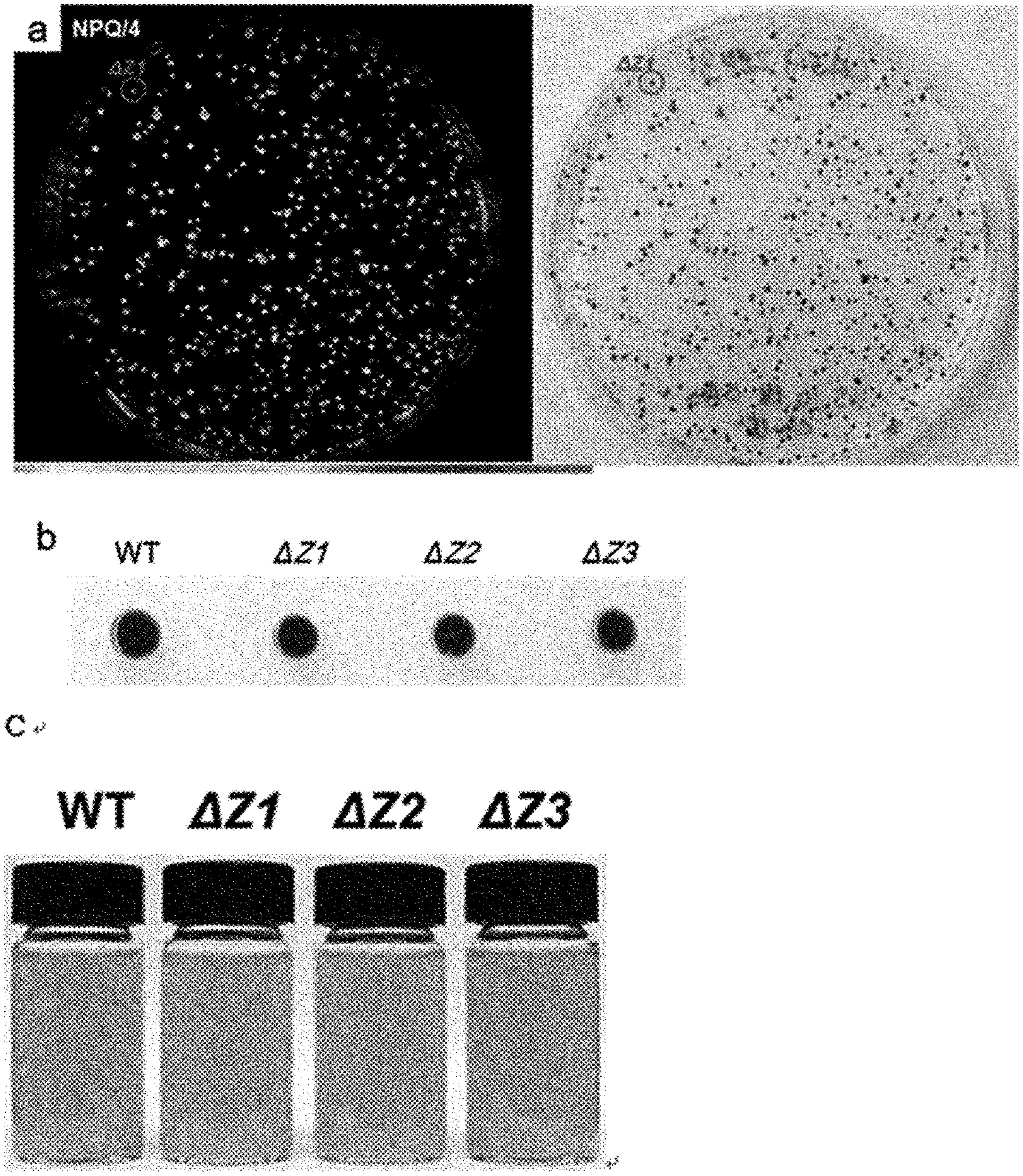

【Figure 7】
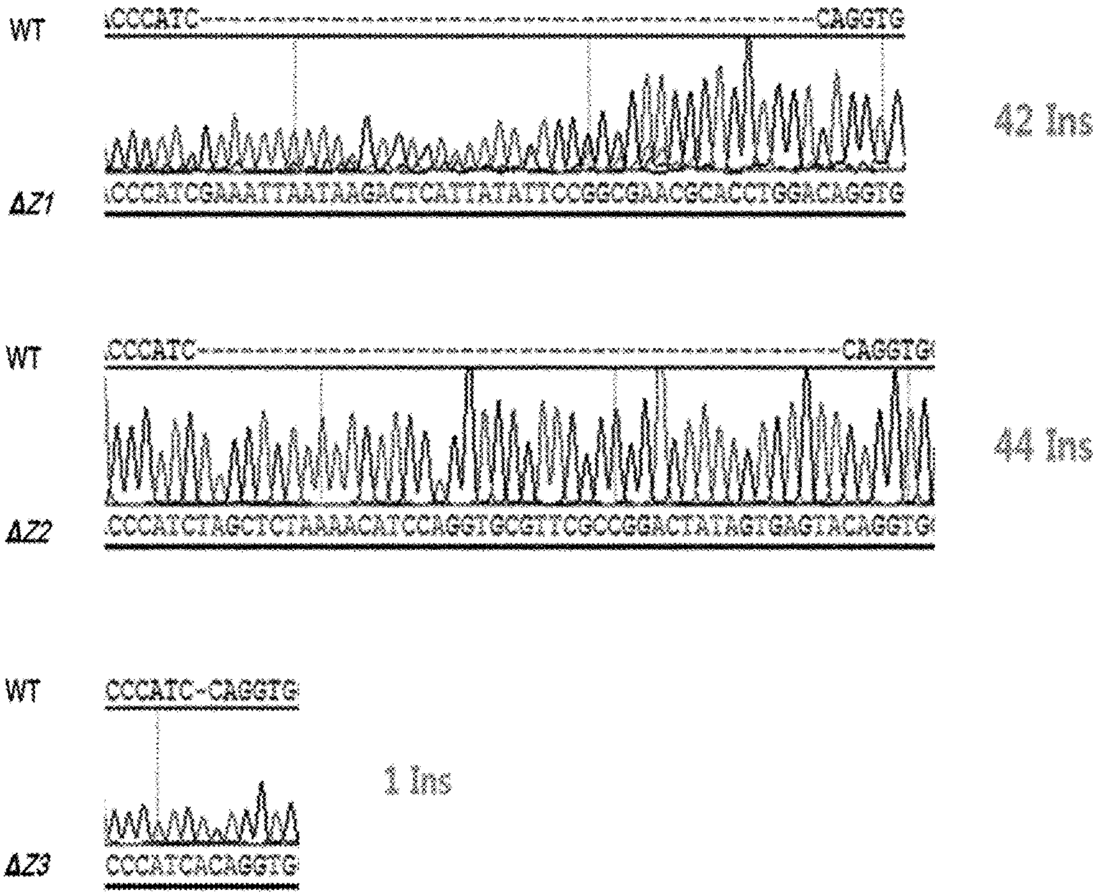

[Figure 8A]
Information on zeaxanthin epoxidase (ZEP) gene of Chlamydomonas wild-type and ZEP genes in ZEP mutants 1, 2, and 3
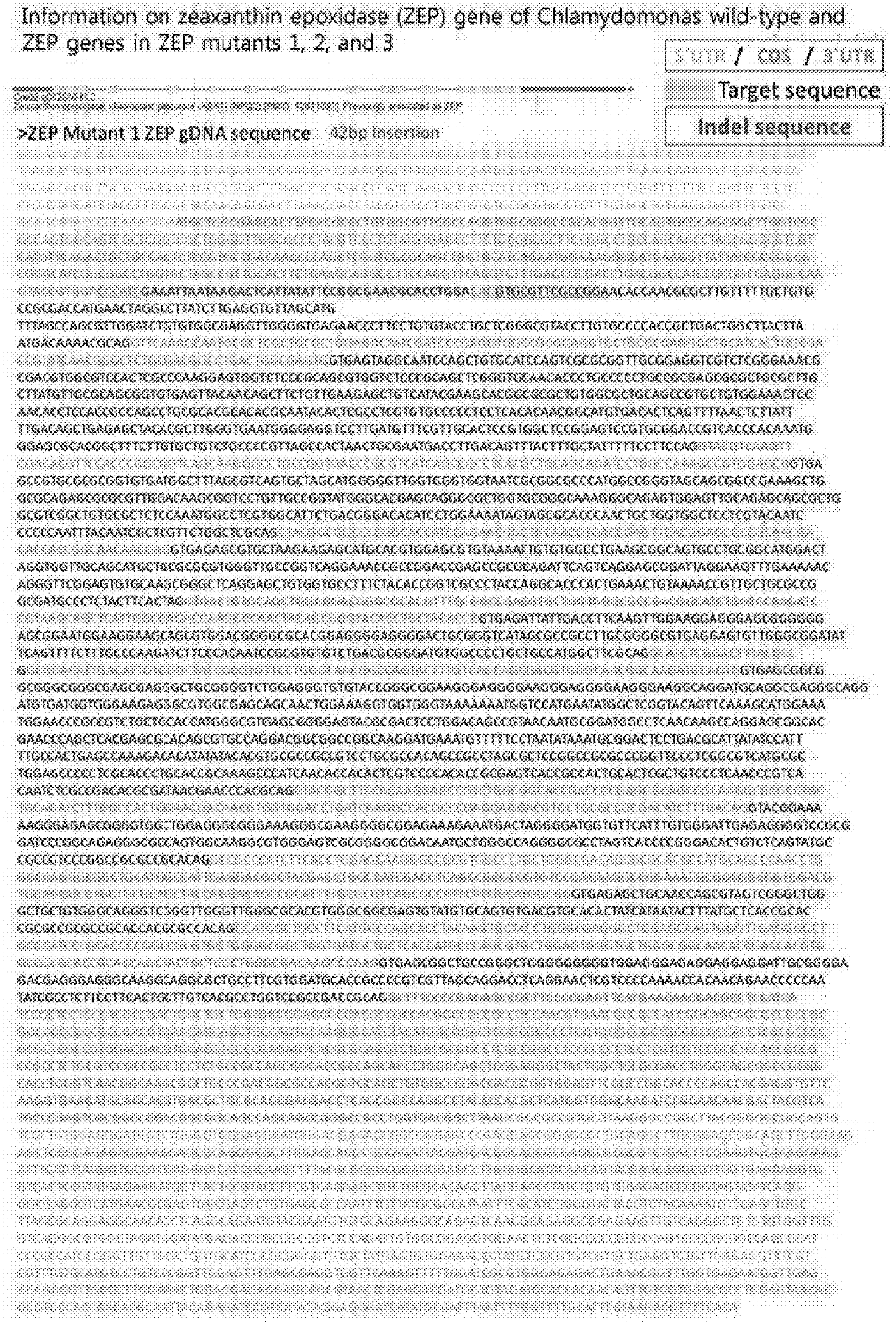

[Figure 8B]

Information on zeaxanthin epoxidase (ZEP) gene of Chlamydomonas wild-type and ZEP genes in ZEP mutants 1, 2, and 3

5'UTR / CDS / 3'UTR

Target sequence

Indel sequence

Cre02.g082550.t1.2
Zeaxanthin epoxidase, chloroplast precursor (ABA1) (NPQ2) [PMID: 12671093]; Previously annotated as ZEP >ZEP Mutant 2 ZEP gDNA sequence 44bp insertion

[illegible] TAGCTCTAAAACATCCAGGTGCGTTCGCCGGACTATAGTGAGTA [illegible] ACACCAACGCGCTTGTTTTTGCTGTG
CCGCGACCATGAACTAGGCCTTATCTTGAGGTGTTAGCATG
TTTAGCCAGCGTTGGATCTGTGTGGCGAGGTTGGGGTGAGAACCCTTCCTGTGTACCTGCTCGGGCGTACCTTGTGCCCCACCGCTGACTGGCTTACTTA
ATGACAAAACGCAG [illegible]
[illegible] GTGAGTAGGCAATCCAGCTGTGCATCCAGTCGCGCGGTTGCGGAGGTCGTCTCGGGAAACG
CGACGTGGCGTCCACTCGCCCAAGGAGTGGTCTCCCGCAGCGTGGTCTCCCGCAGCTCGGGTGCAACACCCTGCCCCCTGCCGCGAGCGCGCTGCGCTTG
CTTATGTTGCGCAGCGGTGTGAGTTACAACAGCTTCTGTTGAAGAGCTGTCATACGAAGCACGGCGCGCTGTGGCGCTGCAGCCGTGCTGTGGAAACTCC
AACACCTCCACCGCCAGCCTGCGCACGCACACGCAATACACTCGCCTCGTGTGCCCCCTCCTCACACAACGGCATGTGACACTCAGTTTTAACTCTTATT
TTGACAGCTGAGAGCTACACGCTTGGGTGAATGGGGAGGTCCTTGATGTTTCGTTGCACTCCGTGGCTCCGGAGTCCGTGCGGACCGTCACCCACAAATG
GGAGCGCACGGCTTTCTTGTGCTGTCTGCCCCGTTAGCCACTAACTGCGAATGACCTTGACAGTTTACTTTGCTATTTTTCCTTCCAG [illegible]
[illegible] GTGA
GCCGTGCGCGCGGTGTGATGGCTTTAGCGTCAGTGCTAGCATGGGGGTTGGTGGGTGGTAATCGCGGCGCCCATGGCCGGGTAGCAGCGGCCGAAAGCTG
GCGCAGAGCGCGCGTTGGACAAGCGGTCCTGTTGCCGGTATGGGCACGAGCAGGGCGCTGGTGCGGGCAAAGGGCAGAGTGGAGTTGCAGAGCAGCGCTG
GCGTCGGCTGTGCGCTCTCCAAATGGCCTCGTGGCATTCTGACGGGACACATCCTGGAAAATAGTAGCGCACCCAACTGCTGGTGGCTCCTCGTACAATC
CCCCCAATTTACAATCGCTCGTTCTGGCTCGCAG [illegible]
[illegible] GTGAGAGCGTGCTAAGAAGAGCATGCACGTGGAGCGTGTAAAATTGTGTGGCCTGAAGCGGCAGTGCCTGCGGCATGGACT
AGGTGGTTGCAGCATGCTGCGCGCGTGGGTTGCCGGTCAGGAAACCGCCGGACCGAGCCGCGCAGATTCAGTCAGGAGCGGATTAGGAAGTTTGAAAAAC
AGGGTTCGGAGTGTGCAAGCGGGCTCAGGAGCTGTGGTGCCTTTCTACACCGGTCGCCCTACCAGGCACCCACTGAAACTGTAAAACCGTTGCTGCGCCG
GCGATGCCCTCTACTTCACTAG [illegible]
[illegible] GTGAGATTATTGACCTTCAAGTTGGAAGGAGGGAGCGGGGGG
AGCGGAATGGAAGGAAGCAGCGTGGACGGGGCGCACGGAGGGGAGGGGACTGCGGGTCATAGCGCCGCCTTGCGGGGCGTGAGGAGTGTTGGGCGGATAT
TCAGTTTTCTTTGCCCAAGATCTTCCCACAATCCGCGTGTGTCTGACGCGGGATGTGGCCCCTGCTGCCATGGCTTCGCAG [illegible]
[illegible] GTGAGCGGCG
GCGGGCGGGCGAGCGAGGGCTGCGGGTCTGGAGGGTGTGTACCGGGCGGAAGGGAGGGGAAGGGAGGGGAAGGGAAGGCAGGATGCAGGCGAGGGCAGG
ATGTGATGGTGGGAAGAGGGCGTGGCGAGCAGCAACTGGAAAGGTGGTGGGTAAAAAAATGGTCCATGAATATGGCTCGGTACAGTTCAAAGCATGGAAA
TGGAACCCGCCGTCTGCTGCACCATGGGCGTGAGCGGGGAGTACGCGACTCCTGGACAGCCGTAACAATGCGGATGGCCTCAACAAGCCAGGAGCGGCAC
GAACCCAGCTCACGAGCGCACAGCGTGCCAGGACGGCGGCCGGCAAGGATGAAATGTTTTTCCTAATATAAATGCGGACTCCTGACGCATTATATCCATT
TTGCCACTGAGCCAAAGACACATATATACACGTGCGCCGCCGTCCTGCGCCACAGCCGCCTAGCGCTCCGGCCGCGCCCGGTTCCCTCGGCGTCATGCGC
TGGAGCCCCCTCGCACCCTGCACCGCAAAGCCCATCAACACCACACTCGTCCCCACACCGCGAGTCACCGCCACTGCACTCGCTGTCCCTCAACCCGTCA
CAATCTCGCCGACACGCGATAACGAACCCACGCAG [illegible]
[illegible] GTACGGAAA
AAGGGAGAGCGGGGTGGCTGGAGGGCGGGAAAGGGCGAAGGGGCGGAGAAAGAAATGACTAGGGGATGGTGTTCATTTGTGGGATTGAGAGGGGTCCGCG
GATCCCGGCAGAGGGCGCCAGTGGCAAGGCGTGGGAGTCGCGGGGCGGACAATGCTGGGCCAGGGGCGCCTAGTCACCCCGGGACACTGTCTCAGTATGC
CGCCGTCCCGGCCGCGCCGCACAG [illegible]
[illegible] GTGAGAGCTGCAACCAGCGTAGTCGGGCTGG
GCTGCTGTGGGCAGGGTCGGGTTGGGTTGGGCGCACGTGGGCGGCGAGTGTATGTGCAGTGTGACGTGCACACTATCATAATACTTTATGCTCACCGCAC
CGCGCCGCGCCGCACCACGCGCCCACAG [illegible]
[illegible] GTGAGCGGCTGCCGGGCTGGGGGGGGGTGGAGGGAGAGGAGGAGGATTGCGGGGA
GACGAGGGAGGGCAAGGCAGGCGCTGCCTTCGTGGATGCACCGCCCCGTCGTTAGCAGGACCTCAGGAACTCGTCCCCAAAACCCACAACAGAACCCCCAA
TATCGCCTCTTCCTTCACTGCTTGTCACGCCTGGTCCGCCGACCGCAG [illegible]

[Figure 8C]

Information on zeaxanthin epoxidase (ZEP) gene of Chlamydomonas wild-type and ZEP genes in ZEP mutants 1, 2, and 3

5'UTR / CDS / 3'UTR

Target sequence

Indel sequence

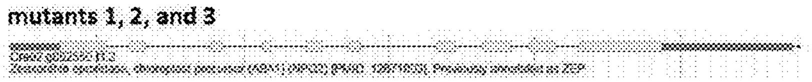

>ZEP Mutant 3 ZEP gDNA sequence 1bp Insertion

GTGCGTTCGCCGGAACACCAACGCGCTTGTTTTTGCTGTGCCGCGACCATGAACTAGGCCTTATCTTGAGGTGTTAGCATG
TTTAGCCAGCGTTGGATCTGTGTGGCGAGGTTGGGGTGAGAACCCTTCCTGTGTACCTGCTCGGGCGTACCTTGTGCCCCACCGCTGACTGGCTTACTTA
ATGACAAAACGCAG
GTGAGTAGGCAATCCAGCTGTGCATCCAGTCGCGCGGTTGCGGAGGTCGTCTCGGGAAACG
CGACGTGGCGTCCACTCGCCCAAGGAGTGGTCTCCCGCAGCGTGGTCTCCCGCAGCTCGGGTGCAACACCCTGCCCCCTGCCGCGAGCGCGCTGCGCTTG
CTTATGTTGCGCAGCGGTGTGAGTTACAACAGCTTCTGTTGAAGAGCTGTCATACGAAGCACGGCGCGCTGTGGCGCTGCAGCCGTGCTGTGGAAACTCC
AACACCTCCACCGCCAGCCTGCGCACGCACACGCAATACACTCGCCTCGTGTGCCCCCTCCTCACACAACGGCATGTGACACTCAGTTTTAACTCTTATT
TTGACAGCTGAGAGCTACACGCTTGGGTGAATGGGGAGGTCCTTGATGTTTCGTTGCACTCCGTGGCTCCGGAGTCCGTGCGGACCGTCACCCACAAATG
GGAGCGCACGGCTTTCTTGTGCTGTCTGCCCCGTTAGCCACTAACTGCGAATGACCTTGACAGTTTACTTTGCTATTTTTCCTTCCAG
GTGA
GCCGTGCCGCGGTGTGATGGCTTAGCGTCAGTGCTAGCATGGGGGTTGGTGGGTGGTAATCGCGGCGCCCATGGCCGGGTAGCAGCGGCCGAAAGCTG
GCGCAGAGCGCGCGTTGGACAAGCGGTCCTGTTGCCGGTATGGGCACGAGCAGGGCGCTGGTGCGGGCAAAGGGCAGAGTGGAGTTGCAGAGCAGCGCTG
GCGTCGGCTGTGCGCTCTCCAAATCGCCTCGTGGCATTCTGACGGGACACATCCTGGAAAATAGTAGCGCACCCAACTGCTGGTGGCTCCTCGTACAATC
CCCCCAATTTACAATCGCTCGTTCTGGCTCGCAGC
GTGAGAGCGTGCTAAGAAGAGCATGCACGTGGAGCGTGTAAAATTGTGTGGCCTGAAGCGGCAGTGCCTGCGGCATGGACT
AGGTGGTTGCAGCATGCTGCGCGCGTGGGTTGCCGGTCAGGAAACCGCCGGACCGAGCCGCGCAGATTCAGTCAGGAGCGGATTAGGAAGTTTGAAAAAC
AGGGTTCGGAGTGTGCAAGCGGGCTCAGGAGCTGTGGTGCCTTTCTACACCGGTCGCCCTACCAGGCACCCACTGAAACTGTAAAACCGTTGCTGCGCCG
GCGATGCCCTCTACTTCACTAG
GTGAGATTATTGACCTTCAAGTTGGAAGGAGGGAGCGGGGGG
AGCGGAATGGAAGGAAGCAGCGTGGACGGGGCGCACGGAGGGGAGGGGACTGCGGGTCATAGCGCCGCCTTGCGGGGCGTGAGGAGTGTTGGGCGGATAT
TCAGTTTTCTTTGCCCAAGATCTTCCCACAATCCGCGTGTGTCTGACGCGGGATGTGGCCCCTGCTGCCATGGCTTCGCAG
GTGAGCGGCG
GCGGGCGGGCGAGCGAGGGCTGCGGGGTCTGGAGGGTGTGTACCGGGCGGAAGGGAGGGGAAGGGAGGGGAAGGGAAGGCAGGATGCAGGCGAGGGCAGG
ATGTGATGGTGGGAAGAGGGGCGTCGCGAGCAGCAACTGGAAAGGTGGTGGGTAAAAAAATGGTCCATGAATATGGCTCGGTACAGTTCAAAGCATGGAAA
TGGAACCCGCCGTCTGCTGCACCATGGGCGTGAGCGGGGAGTACGCGACTCCTGGACAGCCGTAACAATGCGGATGGCCTCAACAAGCCAGGAGCGGCAC
GAACCCAGCTCACGAGCGCACAGCGTGCCAGGACGGCGGCCGGCAAGGATGAAATGTTTTTCCTAATATAAATGCGGACTCCTGACGCATTATATCCATT
TTGCCACTGAGCCAAAGACACATATATACACGTGCGCCGCCGTCCTGCGCCACAGCCGCCTAGCGCTCCGGCCGCGCCCGGTTCCCTCGGCGTCATGCGC
TGGAGCCCCCTCGCACCCTGCACCGCAAAGCCCATCAACACCACACTCGTCCCCACACCGCGAGTCACCGCCACTGCACTCGCTGTCCCTCAACCCGTCA
CAATCTCGCCGACACGCGATAACGAACCCACGCAG
GTACGGAAA
AAGGGAGAGCGGGGTGGCTGGAGGGCGGGAAAGGGCGAAGGGGCGGAGAAAGAAATGACTAGGGGATGGTGTTCATTTGTGGGATTGAGAGGGGTCCGCG
GATCCCGGCAGAGGGCGCCAGTGGCAAGGCGTGGGAGTCGCGGGGCGGACAATGCTGGGCCAGGGGCGCCTAGTCACCCCGGGACACTGTCTCAGTATGC
CGCCGTCCCGGCCGCGCCGCACAG
GTGAGAGCTGCAACCAGCGTAGTCGGGCTGG
GCTGCTGTGGGCAGGGTCGGGTTGGGTTGGGCGCACGTGGGCGGCGAGTGTATGTGCAGTGTGACGTGCACACTATCATAATACTTTATGCTCACCGCAC
CGCGCCGCGCCGCACCACGCGCCACAG
GTGAGCGGCTGCCGGGCTGGGGGGGGGTGGAGGGAGAGGAGGAGGATTGCGGGGA
GACGAGGGAGGGGCAAGGCAGGCGCTGCCTTCGTGGATGCACCGCCCCGTCGTTAGCAGGACCTCAGGAACTCGTCCCCAAAACCCACAACAGAACCCCCAA
TATCGCCTCTTCCTTCACTGCTTGTCACGCCTGGTCCGCCGACCGCAG

【Figure 9】
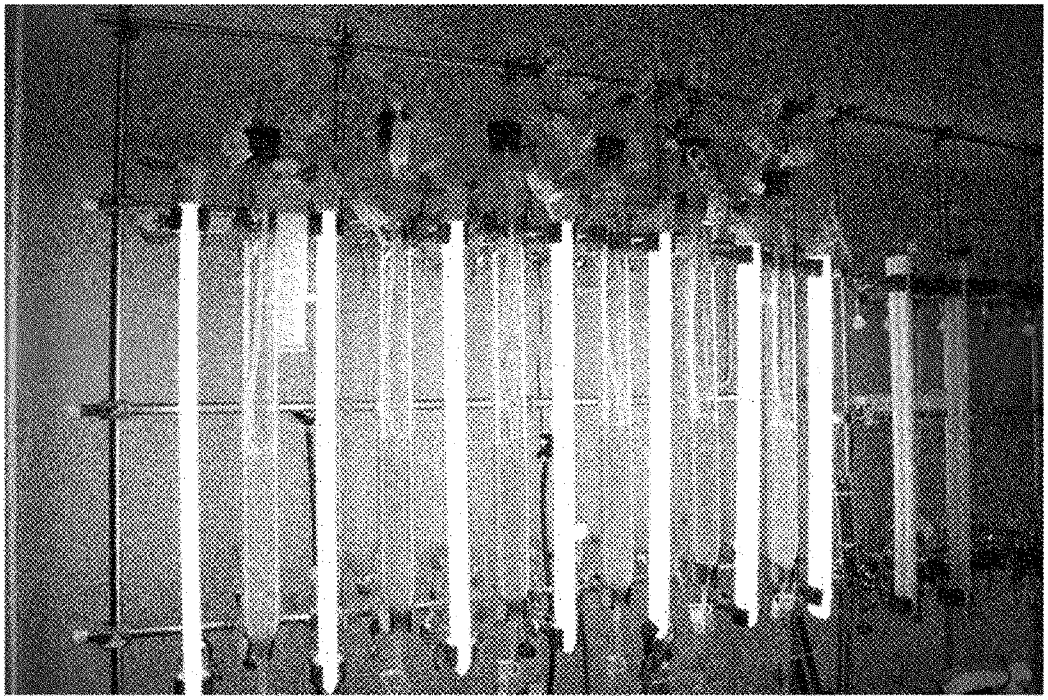
【Figure 10】
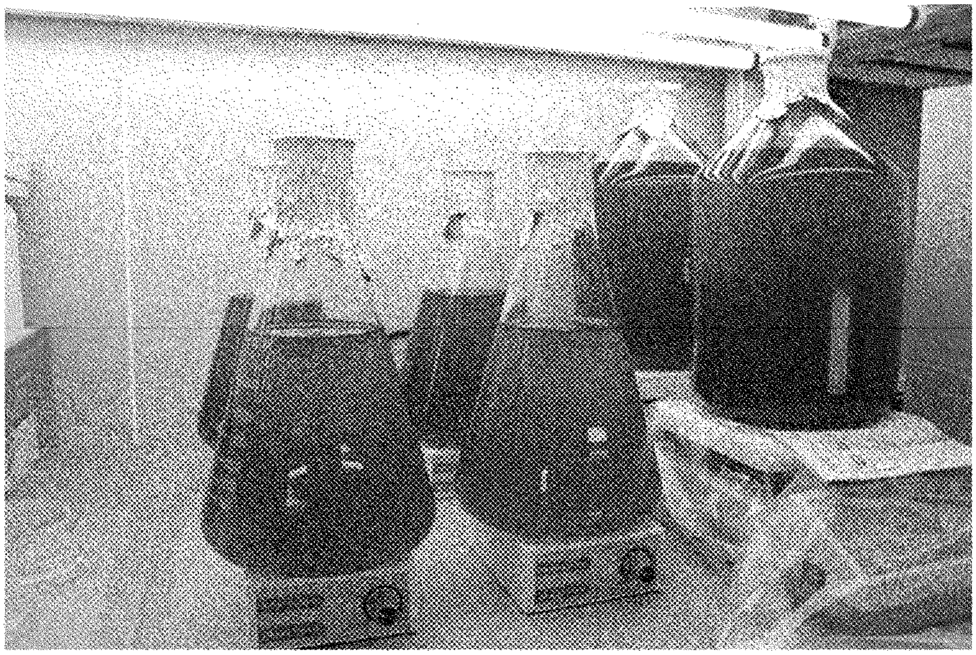

【Figure 11】
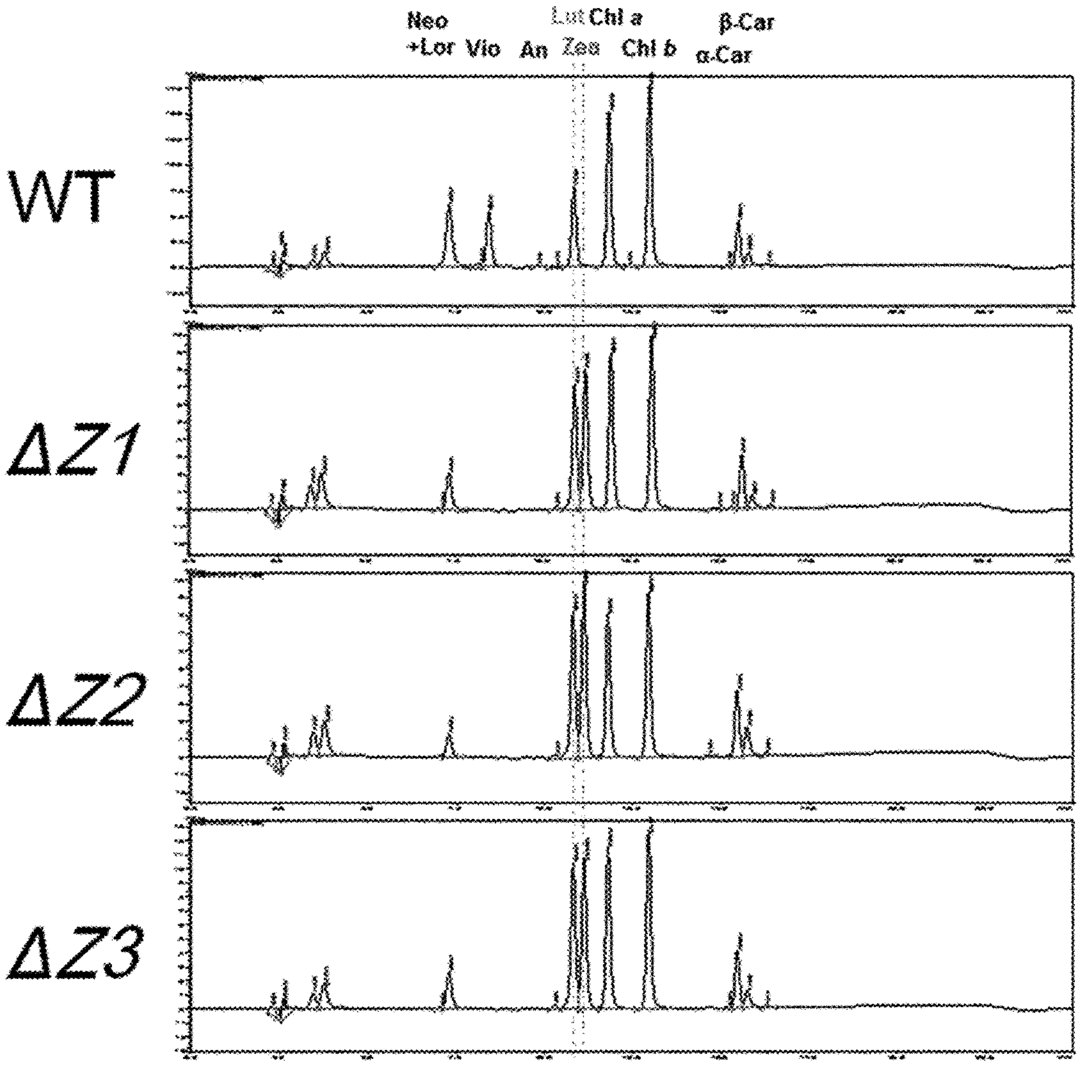

【Figure 12】
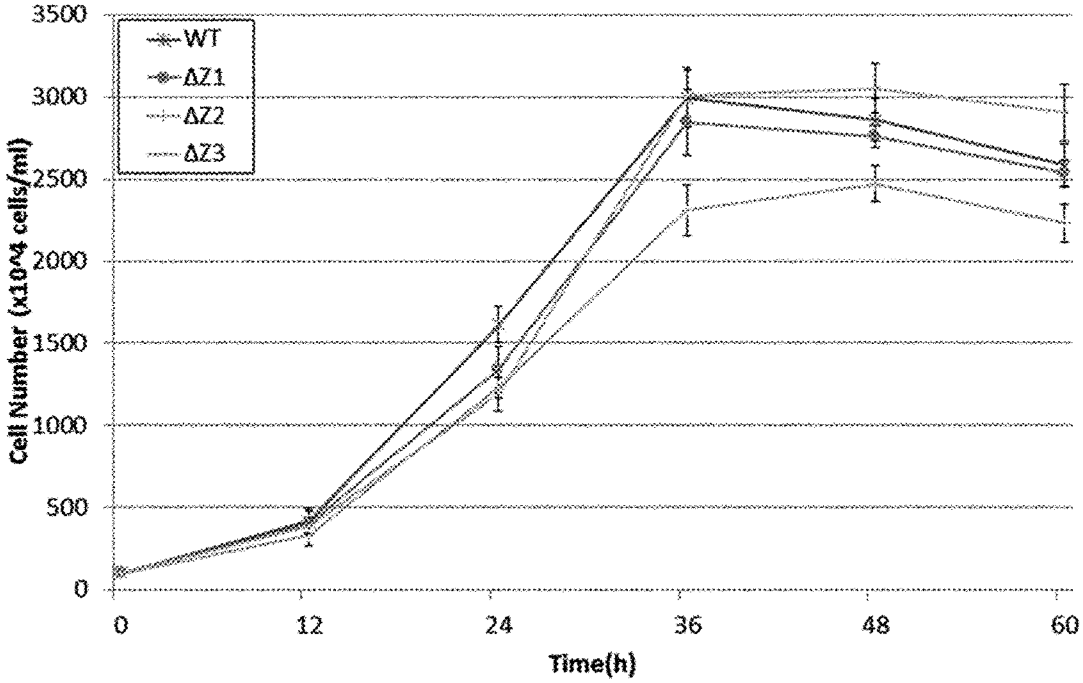
【Figure 13】
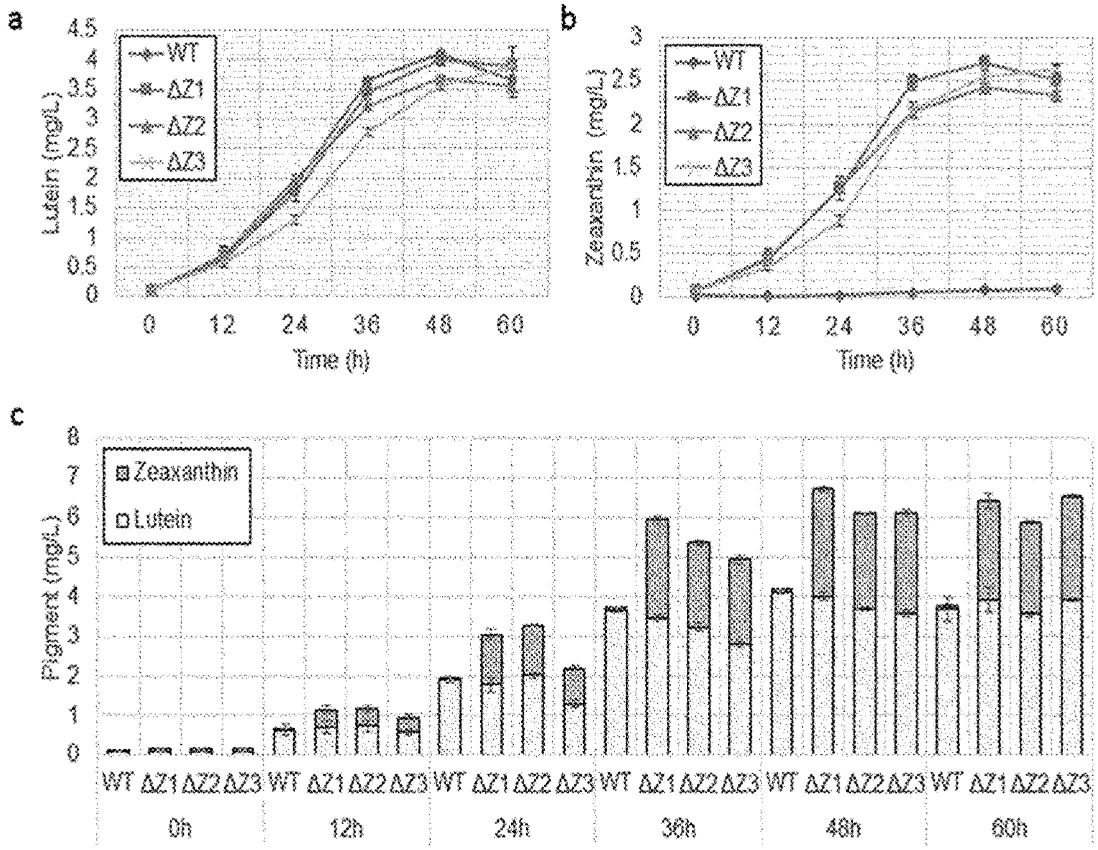

【Figure 14】
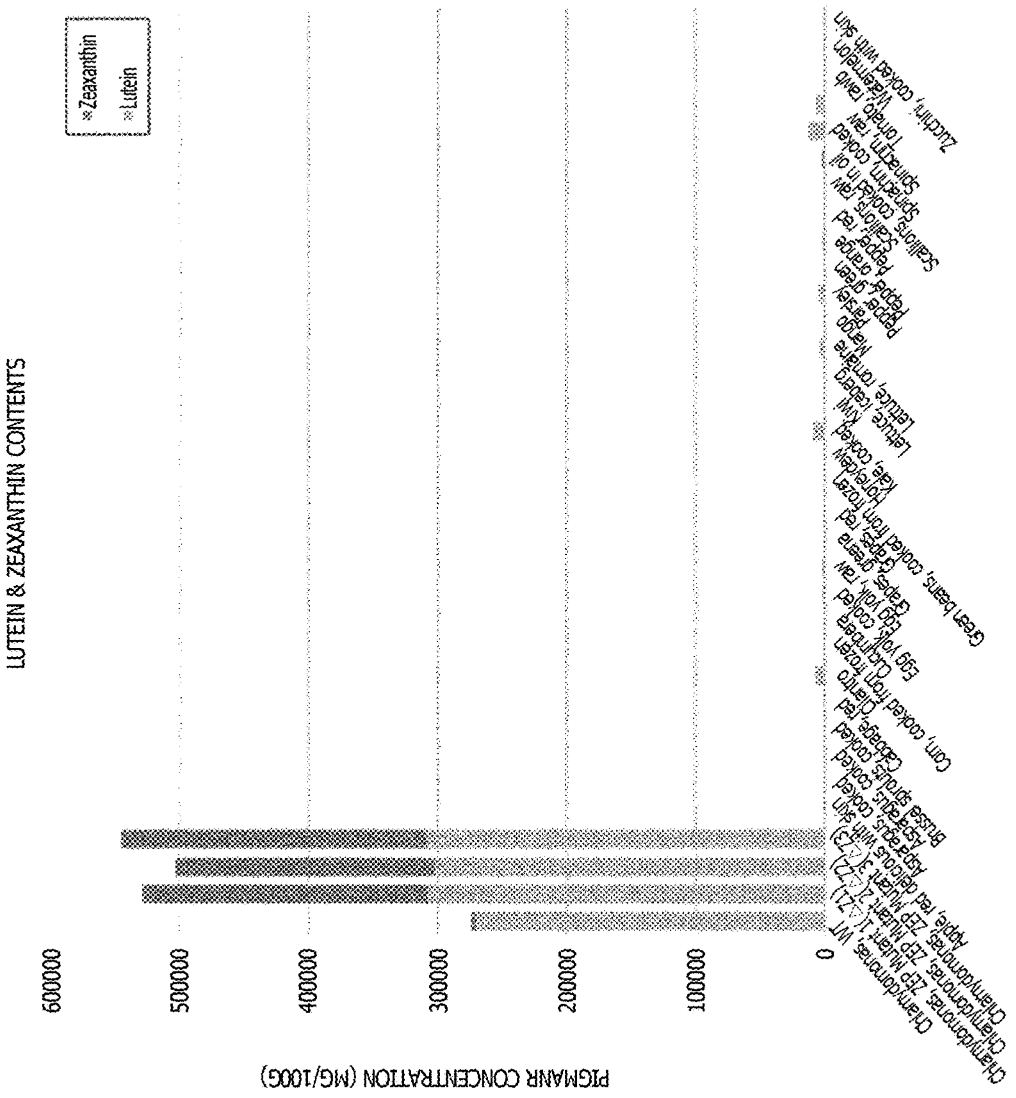

CHLAMYDOMONAS MUTANTS PRODUCED USING RGEN RNP AND METHOD FOR PREPARING PIGMENT USING THE SAME

CROSS-REFERENCE TO RELATED APPLICATION

This application is a Continuation-in-Part (CIP) of PCT Application No. PCT/KR2017/004268, filed Apr. 21, 2017, which claims priority to Korean Patent Application No. 2016-0049439, filed Apr. 22, 2016, and to Korean Patent Application No. 2017-0041761, filed Mar. 31, 2017, and to Korean Patent Application No. 2017-0041762, filed Mar. 31, 2017, the disclosures of which are incorporated herein by reference in their entirety.

TECHNICAL FIELD

The present invention relates to an alga having a pigment producing ability, a dye composition containing the alga, and a method for preparing the pigment.

BACKGROUND ART

Macular degeneration is a disease in which degeneration occurs in the macula which is a nerve tissue located in the center of the inner retina of the eye and causes vision impairment, and since most of the photoreceptors are gathered in the macula and a place where an image of an object is formed is also at the center of the macula, the macula plays a very important role in vision. The most common cause of macular degeneration may be an increase in age (age-related macular degeneration), and is known to be related to family history, race, and smoking. Because the macula is responsible for central vision, if degeneration occurs in the macula, a decrease in vision, central scotoma, metamorphopsia which is a symptom in which things appear distorted, and the like occur. Macular degeneration is largely classified into non-exudative (dry) and exudative (wet), and the non-exudative macular degeneration does not significantly affect vision in most cases, except for the late stage when the atrophy of the retina and the choroid appears, and is a step in which yellow deposits called drusen are seen under the retina, but in the case of the exudative macular degeneration in which subretinal hemorrhage or subretinal fluid, pigment epithelial detachment, and the like appear, when the position of such a lesion is present under the macula or immediately adjacent to the macula, a drop in vision appears from the initial stage. The exudative macular degeneration accounts for about 10 to 20% of the total cases of macular degeneration, but if the exudative macular degeneration is left as it is without being treated, vision rapidly deteriorates, so that many patients will be blind within two years after being diagnosed with the exudative macular degeneration. In order to prevent macular degeneration, it is important to find an abnormality of the macula early through a periodic funduscopic examination and to make an effort so as to reduce the adjustable factors such as obesity, smoking, and hypertension. Since smoking causes damage to choroidal circulation leading to a drop in antioxidant factors in blood and causes choroidal vasoconstriction to cause low oxidative damage, a patient who is at risk of macular degeneration necessarily needs to quit smoking. Further, since a macular pigment (lutein, zeaxanthin) reduces damage caused by aging and serves to maintain a healthy retina, sufficiently ingesting the macular pigment through vegetables and fruits or taking commercialized vitamin supplements can help in the prevention of macular degeneration.

The macular pigment serves to reduce age-related failing eyesight caused in the central part of the retina and prevent retinal tissue damage due to bright light, and representative examples thereof include a xanthophyll as a carotenoid-based oxycarotenoid pigment produced by oxygenation of a carotenoid. Examples of a pigment belonging to xanthophylls include lutein, zeaxanthin, or the like. It is known that lutein acts as an antioxidant that protects the inside of the eyes that is damaged by free oxygen radicals naturally produced in the body, reduces the growth of blood vessels that supply carcinomas to kill cancer cells, and has some effects on prevention of breast cancer, colon cancer, lung cancer, ovarian cancer, and skin cancer.

Animals cannot produce xanthophylls and can obtain xanthophylls only through ingestion of food, but these xanthophylls are present together with chlorophylls and carotenes in the green parts such as leaves, flowers, and fruits of plants. Recently, a health functional food for eye health, including xanthophylls, and the like has attracted attention.

Existing marigold flowers are representative as a raw material for zeaxanthin and lutein, and those extracted from other higher plants has also been studied. In addition, zeaxanthin and lutein are also produced by genetically mutating the pigment synthesis mechanism in bacteria. Studies have also been conducted to obtain these pigments from microalgae. Among these conventional raw materials, marigold flowers have a disadvantage in that it takes a long time to breed flowering plants for production, and have a problem in that the production unit cost is high because the production amount is not large as compared to the land area for production.

In order to solve these problems, the development of zeaxanthin and lutein-producing algae into which a pigment synthesis mechanism is inserted using a bacterial system for replacing a higher plant system was carried out, but there is a problem in that a pigment obtained from bacteria is not suitable for ultimate use as a food additive. In addition, since genetically modified organisms (GMOs) using a genetic insertion technology and the like are not preferred in the domestic market, the GMOs act as a fatal disadvantage in the food additive marker where consumers' perceptions are important, and likewise as in the higher plant system, there is a problem in that a large cost of maintaining a bacterial culture solution, a bioreactor, or the like may be required.

In the case of a method of obtaining these pigments from microalgae, the conventional microalgae are a wild type which is not improved, and have a limitation in being used as optimal producing algae because the content of lutein is constant, but the content of zeaxanthin is very low depending on the amount of light.

REFERENCES OF THE RELATED ART

Patent Document

Korean Patent Application No. 2014-7007656

DISCLOSURE

Technical Problem

An object of the present invention is to provide a method capable of replacing a xanthophyll used as a raw material of a conventional food or a method capable of replacing a conventional raw material production method, and specifically to provide a microorganism having an excellent ability to produce xanthophylls, particularly, lutein and zaexanthin, a composition including the same, and a method for preparing xanthophylls using the same.

Technical Solution

In order to achieve the aforementioned object, the present inventors have made efforts to develop algae capable of solving the insufficient productivity of wild-type or conventionally present microalgae by using other mutations without a genetic recombination method which may be a problem in the food industry, and as a result, developed a mutant having a higher yield of macular pigment than a conventional *Chlamydomonas reinhardtii* alga and identified an optimal method for preparing a pigment using the same, thereby completing the present invention.

In this regard, the present invention provides a *Chlamydomonas reinhardtii* mutant having a ZEP gene mutation in which a base sequence represented by SEQ ID NO: 2 is inserted between a 816th base and a 817th base in a ZEP gene sequence of a *Chlamydomonas reinhardtii* cw15 WT represented by SEQ ID NO: 1 and having an ability to produce xanthophylls.

Further, the present invention provides a *Chlamydomonas reinhardtii* mutant having a ZEP gene mutation in which a base sequence represented by SEQ ID NO: 4 is inserted between a 816th base and a 817th base in a ZEP gene sequence of a *Chlamydomonas reinhardtii* cw15 WT represented by SEQ ID NO: 1 and having an ability to produce xanthophylls.

In addition, the present invention provides a *Chlamydomonas reinhardtii* mutant having a ZEP gene mutation in which a base A is inserted between a 816th base and a 817th base in a ZEP gene sequence of a *Chlamydomonas reinhardtii* cw15 WT represented by SEQ ID NO: 1 and having an ability to produce xanthophylls.

The three *Chlamydomonas reinhardtii* mutants may each have an ability to produce xanthophylls.

The three *Chlamydomonas reinhardtii* mutants may each have an ability to produce one or more pigments selected from the group consisting of lutein and zeaxanthin; and chlorophyll b, chlorophyll a, and β-carotene.

Furthermore, the present invention provides a culture of the *Chlamydomonas reinhardtii* mutant.

Further, the present invention provides a pigment composition including one or more selected from the group consisting of a culture of the mutant, a dry material thereof, and an extract thereof.

In addition, the present invention provides a composition for oral administration, including one or more selected from the group consisting of a culture of the mutant, a dry material thereof, and an extract thereof.

Furthermore, the present invention provides a composition for feed or a feed additive, including one or more selected from the group consisting of a culture of the mutant, a dry material thereof, and an extract thereof.

Further, the present invention provides a composition for a food or food additive, including one or more selected from the group consisting of a culture of the mutant, a dry material thereof, and an extract thereof.

In addition, the present invention provides a method for preparing a pigment using the mutant.

Furthermore, the present invention provides a method for preparing a food or feed raw material, including: culturing the mutant.

Advantageous Effects

Through the present invention, it could be confirmed that three mutants were constructed by using the CRISPR gene scissors technology (RGEN RNPs) without any introduction of an exogenous DNA in a microalga *Chlamydomonas reinhardtii* to knock out a ZEP gene, and the amount of zeaxanthin which is an industrially useful pigment was significantly increased when cellular characteristics of the existing wild type and the three mutants of the present invention were compared with each other. In particular, since a DNA fragment is not likely to be inserted into a target base sequence or a base sequence other than the target, it is expected that the procedure of constructing the mutant is not regulated as a GMO, so that it is expected that the procedure of constructing the mutant can create a big economic effect in terms of an industry which produces lutein and zeaxanthin by using microalgae.

DESCRIPTION OF DRAWINGS

The patent or application file contains at least one drawing executed in color. Copies of this patent or patent application publication with color drawings will be provided by the Office upon request and payment of the necessary fee.

The above and other objects, features and advantages of the present invention will become more apparent to those of ordinary skill in the art by describing in detail exemplary embodiments thereof with reference to the accompanying drawings, in which:

FIG. 1 illustrates a general summary on the techniques and methods applied in the present invention;

FIG. 2 illustrates information on a zeaxanthin epoxidase (ZEP) gene of *Chlamydomonas reinhardtii* cw15 wild type (SEQ ID NO: 1);

FIG. 3 is a summary of five target sequences designed for targeting the *Chlamydomonas reinhardtii* ZEP gene (CACCAGCTGCGCGACCGAGCTGG, SEQ ID NO: 12; GCCGTTGCACTTCTGAAGCAGGG, SEQ ID NO: 13; TCCGGCGAACGCACCTGGATGGG, SEQ ID NO: 14; TGGTGGGCGCCGACGGCATCTGG, SEQ ID NO: 15; CCATGGCTTCGCAGGCATCTCGG, SEQ ID NO: 16) [5 sgRNAs were carefully designed within the half of a coding sequence region of a ZEP gene which is different from any other target sites by 3 nucleotides (nt) in the entire genome and has an out-of-frame score higher than 66 by using Cas-Designer (www.rgenome.net/cas-designer/). The 'coding sequence (CDS) position' refers to a relative position of an excision point in a RNA transcript. a + direction refers to a direction which is the same as a target sequence, that is, means that the same sequence is a sequence of RGEN, and—refers to a direction reverse to the target sequence, that is, a sequence having a reverse complement relationship with each other, which is a sequence bound to the target sequence. The out-of-frame score' indicates the probability of a frame shift-inducing deletion occurring when a cleaved double-stranded DNA is repaired by a microhomology-mediated end joining (MMEJ) pathway. The '# of a target-off site' refers to the number of sequences mismatched throughout the entire genome. The linking of the remaining sgRNA sequence (gttttagagctagaaatagcaagttaaaataaggctagtccgttatcaacttgaaaaagtggcaccgagtcggtgc) (SEQ ID NO: 10) to the target sequence results in the entire sgRNA];

FIG. 4 illustrates mutations of a ZEP gene induced by DNA-free RGEN RNPs [a: RGEN-transfected cell and wild-type mutation (insertion and deletion; indel) frequencies for each sgRNA were measured by targeted deep sequencing. The Indel frequency was measured up to about 0.46%. b: a representative mutant DNA sequence (RGEN3) obtained from the third sgRNA having the highest efficiency observed from the targeted deep sequencing analysis result of a, that is, TCCGGCGAACGCACCTGGATGGG (SEQ ID NO: 11). Various indel patterns identified from the target sequence by the targeted deep sequencing analysis result appearing at the 3 nt upstream of the PAM sequence. The 20-bp target sequence was underlined and the PAM sequence was indicated in bold.]. The depicted nucleotide sequences, listed from top to bottom, are SEQ ID NOs: 17-22;

FIG. 5 illustrates the Cas9 protein sequence used in Example 1 (SEQ ID NO: 9);

FIG. 6 is a set of photographs illustrating morphological characteristics of a *Chlamydomonas reinhardtii* cw15 wild-type alga and *Chlamydomonas reinhardtii* mutants ΔZ1, ΔZ2, and ΔZ3 [a: measurement of chlorophyll (Chl) fluorescence for several hundreds of colonies to study ZEP gene knock-out, b: a photograph of cultivation in a colony state in a solid TAP medium containing agar, c: a photograph illustrating a state when the concentration was adjusted to the same concentration (OD 750=1) after a *Chlamydomonas reinhardtii* cw15 wild-type alga and *Chlamydomonas reinhardtii* mutants ΔZ1, ΔZ2, and ΔZ3 were liquid-cultured in an HS medium];

FIG. 7 identifies variations in target DNA sequences of actual ZEP gene positions in the three ZEP mutants generated by DNA-free RGEN RNPs [a: wildtype (SEQ ID NO: 23), b: ZEP mutant 1(ΔZ1) (SEQ ID NO: 24), c: ZEP mutant 2(ΔZ2) (SEQ ID NO: 25), d. ZEP mutant 3 (ΔZ3) (SEQ ID NO: 26)];

FIG. 8A illustrates information on the ZEP gene of the *Chlamydomonas reinhardtii* mutant ΔZ1 (SEQ ID NO: 3);

FIG. 8B illustrates information on the ZEP gene of the *Chlamydomonas reinhardtii* mutant ΔZ2 (SEQ ID NO: 5);

FIG. 8C illustrates information on the ZEP gene of the *Chlamydomonas reinhardtii* mutant ΔZ3 (SEQ ID NO: 6);

FIG. 9 illustrates autotrophic culture vessels;

FIG. 10 illustrates mixotrophic culture vessels;

FIG. 11 is a set of HPLC analysis graphs illustrating pigment profiles of the *Chlamydomonas reinhardtii* cw15 wild-type and the *Chlamydomonas reinhardtii* mutants ΔZ1, ΔZ2, and ΔZ3 [neo+lor: neoxanthin+loroxanthin, vio: violaxanthin, an: antheraxanthin, lut: lutein, *zea*: zeaxanthin, chl a: chlorophyll a, chl b: chlorophyll b, α-car: α-carotene), and β-car: β-carotene];

FIG. 12 is a graph illustrating the growth curves (the number of cells per volume, cells/ml) of the *Chlamydomonas reinhardtii* cw15 wild-type and the *Chlamydomonas reinhardtii* mutants ΔZ1, ΔZ2, and ΔZ3 over time;

FIG. 13 is a set of graphs comparing the amounts of lutein and zeaxanthin pigments produced by the *Chlamydomonas reinhardtii* cw15 wild-type (WT) and the ZEP knock-out mutants ΔZ1, ΔZ2, and ΔZ3 over time [a: the amount (mg/L) of lutein produced over time, b: the amount (mg/L) of zeaxanthin produced over time, c: the sum (mg/L) of the amounts of lutein and zeaxanthin produced over time]; and FIG. 14 compares the contents of zeaxanthin and lutein among higher plants known to have high contents of zeaxanthin and lutein, the *Chlamydomonas reinhardtii* cw15 wild-type (WT), and the *Chlamydomonas reinhardtii* ZEP knock-out mutants ΔZ1, ΔZ2, and ΔZ3.

BEST MODE

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

However, the present invention may be modified in various forms and may have various forms, so that specific examples and descriptions set forth below are included merely for aiding the understanding of the present invention, and are not intended to limit the present invention to a specific disclosure form. It should be understood that the scope of the present invention includes all the modifications, equivalents, and replacements falling within the spirit and technical scope of the present invention.

Hereinafter, the present disclosure will be described in more detail.

The present relates to a *Chlamydomonas reinhardtii* mutant.

The *Chlamydomonas reinhardtii* is a eukaryote distributed in various environments such as fresh water and oceans as a unicellular green alga (Chlorophyta), and has a doubling time of 6 to 8 hours. Further, the *Chlamydomonas reinhardtii* is one of the microalgae model systems most widely distributed and can be produced in a bioreactor.

The mutant was constructed by using RGEN RNPs which is not a general mutation treatment, that is, the CRISPR gene scissors technology in which exogenous DNAs are not introduced to knock out zeaxanthin epoxidase (ZEP) genes.

The mutant is a mutant (hereinafter, referred to as ΔZ1) having a ZEP gene mutation in which a base sequence (gaaattaata agactcatta tattccggcg aacgcacctg ga) represented by SEQ ID NO: 2 is inserted between a 816th base and a 817th base in a ZEP gene sequence of a *Chlamydomonas reinhardtii* cw15 WT represented by SEQ ID NO: 1. That is, the mutant is a mutant having a ZEP gene mutation represented by SEQ ID NO: 3.

Further, the mutant is a mutant (hereinafter, referred to as ΔZ2 having a ZEP gene mutation in which a base sequence (tagctctaaa acatccaggt gcgttcgccg gactatagtg agta) represented by SEQ ID NO: 4 is inserted between a 816th base and a 817th base in a ZEP gene sequence of a *Chlamydomonas reinhardtii* cw15 WT represented by SEQ ID NO: 1. That is, the mutant is a mutant having a ZEP gene mutation represented by SEQ ID NO: 5.

In addition, the mutant is a mutant (hereinafter, referred to as ΔZ3) having a ZEP gene mutation in which a base A is inserted between a 816th base and a 817th base in a ZEP gene sequence of a *Chlamydomonas reinhardtii* cw15 WT represented by SEQ ID NO: 1. That is, the mutant is a mutant having a ZEP gene mutation represented by SEQ ID NO: 6.

The three *Chlamydomonas reinhardtii* mutants of the present invention each have an ability to produce a pigment, specifically, an ability to produce xanthophylls. Specifically, the three *Chlamydomonas reinhardtii* mutants of the present invention may have an ability to produce lutein and zeaxanthin. More specifically, the three *Chlamydomonas reinhardtii* mutants of the present invention may have an ability to produce one or more pigments selected from the group consisting of lutein and zeaxanthin; and chlorophyll b, chlorophyll a, and β-carotene.

Since the mutant has a significantly high ability to produce zeaxanthin per cell as compared to the conventional *Chlamydomonas reinhardtii* cw15 wild-type and a content of lutein and zeaxanthin which is more than 12 times higher than those of higher plants known to have a high content of lutein and zeaxanthin [see FIG. 14], there is an advantage in that the mutant can be effectively used as an alga for producing xanthophyll.

In a specific exemplary embodiment, it was confirmed that the mutant of the present invention had a significantly increased amount of zeaxanthin produced over time as compared to the *Chlamydomonas reinhardtii* cw15 wild-type (FIG. 13B), so that it could be seen that the mutant of the present invention had mycological properties having an excellent ability to produce xanthophylls, particularly, zeaxanthin, and it was confirmed that the mutant of the present invention could be effectively utilized as a source of producing a xanthophyll pigment by utilizing the mycological properties.

The mutant of the present invention can survive in dim light, and may be cultured under light intensity conditions specifically within a range of 10 to 2,000 μmol photons/$m^2$ s. The mutant cannot photosynthesize in complete darkness which is equal to or less than the dim light conditions, and cell can be damaged by lighting stress under excessive lighting conditions. When the mutant of the present invention is cultured under the conditions, there is an advantage in that the mutant of the present invention has an excellent growth rate while increasing the content of a xanthophyll in the mutant.

The mutant can be appropriately grown within typical growth environments (light intensity conditions, temperature conditions, medium, and the like) of a *Chlamydomonas reinhardtii* alga. Furthermore, since the mutant has an excellent ability to accumulate zeaxanthin even under low light intensity (FIG. 13), the mutant can be industrially and effectively as a xanthophyll pigment-producing microorganism due to the excellent ability to produce a xanthophyll, and the density thereof in a cluster is relatively lower than other algae even under high light intensity, so that the mutant has an effect of having an excellent efficiency of producing a pigment by photosynthesis in a single cell. Specifically, the *Chlamydomonas reinhardtii* wild-type produces almost no zeaxanthin, but the mutant of the present invention has a content of zeaxanthin, which is higher by about 50 times or more than that of the wild-type.

The mutant can be cultured in an environment capable of culturing a general *Chlamydomonas reinhardtii* alga, and specifically, it is possible to use a culture medium capable of culturing an alga under weak light intensity conditions. In order to culture a specific microorganism, the culture medium contains nutritional materials required by a subject to be cultured, that is, a microorganism to be cultured, and may be a culture medium in which a material for a special purpose is additionally added and mixed. The medium also refers to a culture medium or a culture solution, and is a concept encompassing all of the natural medium, the synthetic medium or the selective medium. The *Chlamydomonas reinhardtii* mutant may be cultured according to a typical culture method. For example, the *Chlamydomonas reinhardtii* mutant may be cultured in an HS medium or a TAP medium, which is a photosynthesis medium, and a carbon source may be added. In an exemplary embodiment, it was confirmed that in the culture solution composition environments in Table 1 in the Examples of the present invention, the mutant of the present invention had an excellent ability to produce zeaxanthin.

A pH of the culture medium is not particularly limited as long as the pH is within a range enabling *Chlamydomonas reinhardtii* to survive and be grown, and as an example, a pH of 6 or more, specifically, *Chlamydomonas reinhardtii* can survive within a PH of 6 to a pH of 9, and may have an optimal growth rate at a pH of 7.0 or more and a pH of less than 8.0.

The mutant may be constructed by treating an existing mutagen or using the CRISPR gene scissors technology without introducing an exogenous DNA into a wild-type strain which is not a gene recombinant mutant through introduction of an exogenous gene to directly introduce RGEN RNPs into a target sequence in a ZEP gene.

The *Chlamydomonas reinhardtii* mutant of the present invention can accumulate a pigment, particularly, a xanthophyll-based pigment in the cells, and can include zeaxanthin in an even higher content among the pigments, so that the alga is cultured, and thus can be effectively used as a raw material for a food, feed, a medicine, and the like.

In this regard, the present invention relates to a culture of the *Chlamydomonas reinhardtii* mutant.

In the present invention, "a culture" refers to a medium in which a specific microorganism is cultured, that is, a post-culture medium, and the culture refers to a culture including the *Chlamydomonas reinhardtii* mutant. Further, the culture refers to a culture including all of the concentrate of the culture where a post-culture medium is subjected to processing such as concentration and drying, or the dry material of the culture. The culture can include a byproduct thereof, the preparation thereof is not limited, and as an example, the culture may be a liquid or a solid.

In order to culture a specific microorganism, the medium contains nutritional materials required by a subject to be cultured, that is, a microorganism to be cultured, and may be a medium in which a material for a special purpose is additionally added and mixed. The medium also refers to a culture medium or a culture solution, and is a concept encompassing all of the natural medium, the synthetic medium or the selective medium. A pH of the medium may be more than a range in which a *Chlamydomonas reinhardtii* mutant can be grown, and may be a pH of 6 or more as an example, and preferably a pH of 6 to 9.

Further, the present invention relates to a composition including one or more selected from the group consisting of the *Chlamydomonas reinhardtii* mutant of the present invention, a culture of the alga, a dry material thereof, and an extract thereof.

The composition may be used for improving the health of a human and an animal.

Since the mutant of the present invention has characteristics of producing a xanthophyll-based pigment including zeaxanthin and lutein and accumulating the pigment in vivo, the composition may be a pigment composition or a xanthophyll pigment composition in this regard.

The pigment composition may be a composition in which zeaxanthin is included in an amount of 5 to 15 parts by weight based on 100 parts by weight of the total pigments included in the composition. According to an exemplary embodiment of the present invention, as a result of measuring the content of zeaxanthin in the total pigments per each cell of the *Chlamydomonas reinhardtii* wild-type alga and the *Chlamydomonas reinhardtii* mutant, it could be confirmed that the *Chlamydomonas reinhardtii* mutant had a significantly high content of zeaxanthin in the pigment even when compared to the wild-type (FIG. 13C).

The pigment composition may be used as a raw material for a food or feed, and may be used as a preparation for oral administration.

Accordingly, a pigment composition or xanthophyll pigment composition including the composition or extract may be a composition for oral administration, in that the pigment composition or xanthophyll composition included in a food, a medicine, feed, or the like may be supplied via an oral route.

The composition for oral administration may be included in a formulated oral preparation by using a method publicly known in the art, such as a powder, a granule, a tablet, a pill, a sugar-coated tablet, a liquid, a gel, a syrup, a slurry, and a suspension. For example, for the oral preparation, a tablet or a purified material of sugar may be obtained by blending an active ingredient with a solid excipient, pulverizing the same, adding a suitable auxiliary agent thereto, and then processing the same into a granular mixture. Examples of a suitable excipient include sugars including lactose, dextrose, sucrose, sorbitol, mannitol, xylitol, erythritol, maltitol, and the like, starches including corn starch, wheat starch, rice starch, potato starch, and the like, celluloses including cellulose, methyl cellulose, sodium carboxymethyl cellulose, hydroxypropylmethyl cellulose, and the like, and fillers such as gelatin and polyvinylpyrrolidone. In addition, a crosslinked polyvinylpyrrolidone, agar, alginic acid, sodium alginate, or the like may be added as a disintegrating agent in some cases.

Furthermore, the composition can be added in order to achieve a purpose use which is special for a food or feed, and thus may be a food composition, a composition for a food additive, a feed composition or a composition for a feed additive. When the composition is used for feed or a food, health in the body can be maintained or strengthened by a xanthophyll pigment, particularly, zeaxanthin and lutein produced by the *Chlamydomonas reinhardtii* mutant and accumulated in the cells. Specifically, the zeaxanthin and lutein can prevent or alleviate degeneration of the macula, and the like as a macular pigment, and thus are effective for preventing or alleviating eye disorders related to the macular degeneration. More specifically, since the zeaxanthin and lutein have effects of strengthening or maintaining eye health; preventing or alleviating the macular degeneration; preventing or alleviating deterioration in eye function; alleviating or preventing damage to the retina; suppressing aging; maintaining retinal health; reducing the risk of developing the macular degeneration; or preventing or alleviating failing eyesight, the feed or food composition may be used for the use of preventing or alleviating the symptoms or the effects.

In the present invention, "for an additive" includes all food compositions as long as the food composition is a constitution in which ingredients other than the main ingredient are added to a food or feed, and a specific example thereof may be an effectively active material having functionality in a food or feed or a food additive defined by the Ministry of Food and Drug Safety of Republic of Korea to be added for coloring, preservation, and the like in a processed food.

The food may be a health functional food. More specifically, the food may be a food functional food for eye health.

The food, the food additive, the feed or the composition for a feed additive may further include other effective ingredients within a range not impairing the activity of the *Chlamydomonas reinhardtii* mutant of the present invention, a culture of the mutant, a dry material thereof, and an extract thereof. Further, it is possible to further include an additional ingredient such as a carrier.

In the present invention, a composition for feed may be prepared in the form of fermented feed, blended feed, a pellet, silage, and the like. The fermented feed may be prepared by including the *Chlamydomonas reinhardtii* mutant of the present invention, a dry fungus body of the mutant, a culture of the mutant, and an extract thereof, and additionally include various microbial bacteria or enzymes.

The blended feed may be prepared by including various types of general feed, the mutant of the present invention, a dry fungus body of the mutant, a culture of the alga, and an extract thereof and mixing the mixture. A feed in the form of a pellet may be prepared by formulating the fermented feed or blended feed with a pellet machine. The silage may be prepared by mixing silage with a *Chlamydomonas reinhardtii* mutant, a dry fungus body of the mutant, a culture of the mutant and/or an extract thereof, but the use of the composition of the present invention is not limited thereto.

The composition may be mixed with a carrier and a flavoring typically used in the food or pharmaceutical field and may be prepared and administered in the form of a tablet, a troche, a capsule, an elixir, a syrup, a powder, a suspension, a granule, or the like. As the carrier, it is possible to use a binder, a lubricant, a disintegrating agent, an excipient, a solubilizing agent, a dispersing agent, a stabilizing agent, a suspending agent, and the like. As an administration method, an oral, parenteral, or application method may be used, but preferably, it is preferred that the composition is orally administered. In addition, an administration dose may be appropriately selected depending on the absorption degree, the inactivation rate and the excretion rate of an active ingredient in the body, and age, gender, status, and the like of a person to be treated. A pH of the composition can be easily changed depending on the production conditions and the like of medicine, food, and the like in which the composition is used.

The composition may include any one selected from the group consisting of a *Chlamydomonas reinhardtii* mutant, a culture of the mutant, a dry material thereof, and an extract thereof in an amount of 0.001 to 99.99 wt %, preferably 0.1 to 99 wt %, based on the total weight of the composition, and the content of an active ingredient may be appropriately adjusted depending on the method for using the composition and the purpose of using the composition.

The *Chlamydomonas reinhardtii* mutant may be included as it is or in a dried form in the composition, and the culture of the alga may be included in a concentrated or dried form in the composition. Furthermore, the dry material refers to a dried form of the alga or the culture thereof, and may be in the form of a powder prepared by lyophilization, and the like.

Further, the extract refers to an extract obtained by extracting a product from the *Chlamydomonas reinhardtii* mutant of the present invention, a culture solution thereof, or a dry material thereof, and includes an extract using a solvent, and the like, and an extract obtained by crushing the *Chlamydomonas reinhardtii* mutant of the present invention. Specifically, the extract may be an extract obtained by extracting and separating a pigment accumulated in the cells of the *Chlamydomonas reinhardtii* mutant of the present invention by a physical or chemical method.

The extraction procedure may be carried out by a typical method, and as an example, a target pigment may be extracted by adding an extraction solvent to the *Chlamydomonas reinhardtii* mutant of the present invention, homogenizing the resulting mixture, and then crushing the fungus body. After the extraction, a crushed material of the alga may be removed through centrifugation, and the extraction solvent may be removed by a method such as distillation under reduced pressure. In addition, the extraction procedure may further include a typical purification process. The aforementioned pigment has a property of being insoluble in water, and thus can be more easily extracted from the alga of the present invention.

Since the *Chlamydomonas reinhardtii* mutant of the present invention has an excellent ability to produce a xanthophyll, particularly zeaxanthin at low light intensity, a compound including the mutant and a byproduct thereof has effects of improving body activity, maintaining body functionality, and preventing deterioration in body functionality. Specifically, since the xanthophyll pigment is known to have an effect of suppressing macular degeneration, antioxidant and anticancer effects, and the like, the composition of the present invention may be used as a raw material included in a food, a health functional food, a medicine, feed, and the like for the use of maintaining body health, specifically, maintaining the body function with which the xanthophyll pigment is associated, preventing deterioration in body function, or improving the body function.

Furthermore, another object of the present invention is to provide a method for preparing a pigment using the *Chlamydomonas reinhardtii* mutant of the present invention.

Further, still another object of the present invention is to provide a method for preparing a food or feed raw material, including: culturing the *Chlamydomonas reinhardtii* mutant of the present invention.

When the *Chlamydomonas reinhardtii* mutant of the present invention is used, an amount of xanthophylls accumulated in the algae to be cultured may be increased, so that the supply of a raw material industrially used, and the like may be efficiently carried out.

The preparation method may include culturing the *Chlamydomonas reinhardtii* mutant of the present invention.

In addition, the preparation method may further include: separating the *Chlamydomonas reinhardtii* mutant of the present invention from the culture, after the culturing of the *Chlamydomonas reinhardtii* mutant of the present invention.

The separated algae may be further subjected to a processing step including drying.

Furthermore, the preparation method may further include: extracting a pigment from the *Chlamydomonas reinhardtii* mutant of the present invention, a concentrate of the culture, or a dry material of the culture.

The culturing may be carried out in a medium under a pH condition of 6.0 to 8.0. Further, the culturing may be carried out under weak lighting conditions, specifically, under light intensity conditions within a range of 10 to 2,000 μmol photons/$m^2$ s. The *Chlamydomonas reinhardtii* mutant of the present invention has an excellent ability to produce a pigment even at low light intensity, and thus may increase the content of xanthophylls in the body, so that an excellent accumulation of xanthophylls may be achieved without inputting energy at high light intensity, and as a result, the *Chlamydomonas reinhardtii* mutant of the present invention may be industrially and effectively used.

The extraction may be carried out by a typical method such as a method for extracting a pigment from microorganisms, and examples thereof include an enzyme method, an ultrasonic extraction method, a mechanical extraction method, and the like, and are not limited thereto.

The preparation method may further include, in addition to the culturing step, a concentrating step of increasing the content of the alga after the culturing and a drying step of drying the alga subjected to the concentrating step by further reducing moisture in the alga. However, the concentrating step or the drying step is not necessarily needed, and may be generally carried out by using a concentrating and drying method, and a machine typically used in the field to which the present invention belongs.

The preparation method may be carried out by further including a purification step after the extracting step, and the purification step may be carried out by a typical purification method in the field to which the present invention belongs.

Xanthophylls prepared through the concentrating or drying step may be used as a raw material for a food, a health functional food, a cosmetic, a medicine, or the like.

The method for preparing xanthophylls may be carried out by adopting other methods within a range not impairing the effects of the present invention.

The contents on the mutant and the composition may also be applied mutatis mutandis to the preparation method of the present invention.

Hereinafter, the present invention will be described in detail through the Examples. However, the following Examples are only for exemplifying the present invention, and the scope of the present invention is not limited to the following Examples. The present Examples are provided to make the disclosure of the present invention perfect and to make a person skilled in the art to which the present invention belongs perfectly comprehend the scope of the present invention, and the present invention is defined only by the scope of the claims.

EXAMPLES

Example 1: Construction of ZEP Gene Knock-Out Mutant

In order to target a ZEP gene of *Chlamydomonas reinhardtii* (phytozome: Cre02.g082550 or NCBI: AY211267.1) [https://phytozomejgi.doe.gov/pz/portal.html#!gene?search=1&detail=1&method=4614&searchText=transcriptid:30785220, present at a position of 1244277-1250969 in chromosome #2], for an sgRNA, five sgRNAs which allow the induction of a microhomology-driven frameshift mutation by using Cas-Designer (www.rgenome.net) were designed, and were synthesized through an in vitro transcription method. FIG. 3 is a description on the target sequences of the five sgRNAs constructed for targeting the ZEP gene. A Cas9 protein was prepared by expressing a recombinant Cas9 protein using *E. coli*, and performing purification. A *Chlamydomonas reinhardtii* cw15 mt-wild-type (CC-4349) used in the experiment was secured through the *Chlamydomonas* Resource Center (www.chlamycollection.org) [http://www.chlamycollection.org/product/cc-4349-cw15-mt-goodenough-330a/]. The *Chlamydomonas* cells were put into a 25° C. 50-ml flask containing a TAP medium [see Table 2], and were cultured while being irradiated with light using a fluorescence lamp at a light intensity of 70 uE and being shaken at 90 rpm. The concentration of the cells was measured by using a spectrophotometer, and cells during a period of actively culturing to an $OD_{750}$ of approximately 0.3 to 0.5 were used. In order to make a complex of RNPs, 200 ug of the Cas9 protein (FIG. 5, SEQ ID NO: 9) was mixed with 140 ug of the sgRNA (SEQ ID NO: 8) in nuclease-free water, and incubated at room temperature for 10 minutes. After the complex of the bound RNPs was transformed along with $50 \times 10^4$ *Chlamydomonas reinhardtii* cw15 mt-wild-type (CC-4349) cells through (voltage 600 V, Capacity 50 g) electric shock in a 4 mm electroporation cuvette by using a Biorad Gene Pulser Xcell™ electroporation system, the complex was subjected to gDNA extraction after dark incubation for 12 hours, and analyzed by performing targeted deep sequencing, and a single colony was obtained by diluting a part of the complex with 2,000 cells and streaking and spreading the diluted solution on a TAP agar plate. FIG. 4 is a result identifying the mutation of the ZEP gene, which was induced by RGEN-RNPs due to the targeted deep sequencing. The mutation of a target gene was identified by separating the single colony induced by the third sgRNA (0.456%) where the transformation efficiency was at the highest level. (FIG. 4*b* illustrates the data of the targeted deep sequencing and of an experiment in which when the entire cells are collected and gDNAs are extracted and analyzed after the transformation experiment using the RNPs, all the mutations occurring in the DNA strands of a target site for the entire cells are analyzed, and the pattern and frequency thereof can be seen. That is, FIG. 4*b* illustrates patterns of the mutation actually identified at the target site through the targeted deep sequencing, but it is difficult to find out a big size change such as insertion of 42 bp or more by a principle of the targeted deep sequencing, and there may be a difference from a single colony actually obtained)

After the ZEP specific knock-out mutant was produced in this manner by using DNA-free RGEN RNPs, the Chl fluorescence with respect to all the cells was measured in the petri dish, and several estimated ZEP knock-out cell lines were selected. A circular shape indicates an estimated ZEP knock-out mutant grown on a TAP agar medium under dim light (50 μmol photons/$m^2$ s) conditions NPQ/4 images were measured by Imaging PAM (Walz). Unicellular colonies of the wild-type (WT) and AZEP mutant cell lines were grown on a minimum agar medium under dim light (50 μmol photons/$m^2$ s) conditions [FIGS. 6*a* and 6*b*]. Among the thus-identified colonies, three mutants (ΔZ1, ΔZ2, and ΔZ3) where the content of the macular pigment was increased were selected, and a change in target DNA sequence at the actual position of the ZEP position was identified from the three ZEP mutants generated by RGEN RNPs through Sanger sequencing [FIG. 7].

As illustrated in FIG. 6*b*, it could be confirmed that the colonies of the *Chlamydomonas reinhardtii* cw15 wild-type and the mutants ΔZ1, ΔZ2, and ΔZ3 were grown in forms and sizes similar to one another on the TAP agar plate under the same light intensity conditions. Further, in the case of the cells liquid-cultured through photosynthesis in an HS medium, it can be confirmed that at the same concentration of the cells, the *Chlamydomonas reinhardtii* wild-type exhibits a striking green color, whereas the mutants ΔZ1, ΔZ2, and ΔZ3 exhibit a green color similar to a grass color tone [FIG. 6*c*].

Among the selected mutants, the mutant Z1 was named as *Chlamydomonas reinhardtii* ZEP mutant 1 (ΔZ1), and the mutant was deposited at the Korean Collection for Type Cultures (KCTC), Korea Research Institute of Bioscience & Biotechnology on Mar. 22, 2017 and given Accession No. KCTC 13230BP.

Example 2: Culturing of Mutant

1) Autotrophic Culture

In the case of an autotrophic culture in which the mutant was cultured in a state where an external carbon source was not supplied and by using only photosynthesis, the mutant was cultured in an HS medium which is a minimum medium by supplying 5% $CO_2$. After a medium having the composition as in the following Table 1 was produced, the medium was autoclaved and prepared, and the growth was initiated by making the concentration become $10^6$ cells/mL in the culture solution using cells in an active growth stage. A culture vessel was supplied with bubbles from beneath using a column made of glass as in FIG. 9, and was irradiated with light using a fluorescence lamp at a light intensity of 200 uE from both sides.

TABLE 1

| HS Media Ingredients | Con. in culture solution (nM or μM)) |
|---|---|
| Buffer and Major Ingredients (nM) | |
| $NH_4Cl$ | 9.345 |
| $MgSO_4$•$7H_2O$ | 0.08 |
| $CaCl_2$•$2H_2O$ | 0.07 |
| $K_2HPO_4$ | 8.265 |
| $KH_2PO_4$ | 5.29 |
| Trace Ingredients (μM) | |
| $ZnSO_4$•$7H_2O$ | 765 |
| $H_2BO_2$ | 922 |
| $MnCl_4$•$4H_2O$ | 511 |
| $CoCl_2$•$6H_2O$ | 7 |
| $CuSO_4$•$5H_2O$ | 126 |
| $(NH_4)_6Mo_2O_{24}$•$4H_2O$ | 18 |
| $FeSO_4$•$7H_2O$ | 18 |
| EDTA disodium salt | 134 |
| Others | |
| Carbon Source | 5% $CO_2$ bubble, 80 cc/min |
| pH in Culture Solution | 7.0 |
| Light Intensity | 200 uE |

2) Mixotrophic Culture

In the case of performing a mixotrophic culture where the mutant was cultured by supplying both photosynthesis and a carbon source, the mutant was cultured by adding acetic acid to a TAP medium. After a medium having the composition as in the following Table 2 was produced, the medium was autoclaved and prepared, and the growth was initiated by making the concentration become $10^6$ cells/mL in the culture solution using cells in an active growth stage. For the culture vessels, the mutant was cultured at large volumes by using a flask or bottle made of glass as in FIG. 10, and was stirred by using a magnetic bar. The mutant was together irradiated with light using a fluorescence lamp at a light intensity of 70 uE.

TABLE 2

| TAP Media Ingredients | Con. in culture solution (nM or μM)) |
|---|---|
| Buffer and Major Ingredients (nM) | |
| $NH_4Cl$ | 7.5 |
| $CaCl_2$•$2H_2O$ | 0.675 |
| $MgSO_4$•$7H_2O$ | 0.8 |
| $K_2HPO_4$ | 0.62 |
| $KH_2PO_4$ | 0.41 |
| Trace Ingredients (μM) | |
| EDTA•$2H_2O$ | 135 |
| $FeSO_4$•$7H_2O$ | 18 |
| $ZnSO_4$•$7H_2O$ | 75 |
| $H_2BO_2$ | 185 |
| $MnCl_2$•$4H_2O$ | 26 |
| $CuCl_2$•$2H_2O$ | 6.5 |
| $Na_2MoO_4$•$2H_2O$ | 5.5 |
| $CoCl_2$•$6H_2O$ | 6.5 |

TABLE 2-continued

| TAP Media Ingredients | Con. in culture solution (nM or μM)) |
| --- | --- |
| Others | |
| Carbon Source | Glacial acetic acid, 1ml/L |
| Tris | 2.42 g/L |
| pH in Culture Solution | 7.2 |
| Light Intensity | 20 uE |

Example 4: Pigment Analysis of Mutant and Identification of Growth Characteristics 1) Pigment Analysis of Mutant After a separation into a single colony as in Example 1, the mutant was continuously cultured, and a pigment analysis of each colony was carried out by using HPLC.

Specifically, the separated single colonies were cultured in a TAP medium under 70 μmol photons/$m^2$ s conditions for 3 days, and the specific culture conditions were carried out as under the culture conditions in 2) of Example 2. From the harvested alga, a pigment was extracted by using 80% acetone, and a centrifuged supernatant was filtered again by using a nylon filter, and then injected into an HPLC and analyzed.

Specifically, in order to separate the pigment, the total flow rate of the solvent was set at 1.2 mL per minute, and Tris with a pH of 8.0 and acetonitrile were each uniformly decreased from 14% and 84% to 0% from the 0th minute to the 15th minute, and methanol and ethyl acetate were increased starting from 2% to 68% and 32%, respectively, up to the 15th minute. Thereafter, this solvent ratio was maintained as it was for 3 minutes (from the 15th minute to the 18th minute), and then the ratio of each solvent was returned to the ratio at the start for 1 minute (from the 18th minute to the 19th minute), and then a post-run was performed while maintaining the solvent ratio as it was for the remaining 6 minutes. Shimadzu LC-20A Prominence manufactured by Shimadzu Company was used as a pump, Watera Spherisorb TMSS (DS1 4.6×250 mm, 5 μm Cartridge Column, USA) was used as a column, and the temperature of the column was maintained at 40° C. Data was analyzed by using a photodiode array detector (SPD-M20A, Shimadzu) as a detector, and the concentrations were obtained by using a standard curve which quantified a carotenoid and chlorophylls a and b purchased from Agern Alle, Horsholm, Denmark (DHL) as a standard from the result in which carotenoid pigments including zeaxanthin and chlorophyll a were detected at 445 nm and 670 nm, respectively.

FIG. 11 illustrates HPLC analysis graphs illustrating a pigment profile of each alga, and FIG. 13 illustrates a set of graphs which quantitatively analyze the contents of zeaxanthin and lutein of each alga grown under 200 μmol photons/$m^2$ s using HPLC.

2) Identification of Growth Rate

In order to compare the cell proliferation rates and final growth amounts of the wild-type *Chlamydomonas reinhardtii* alga and the mutants ΔZ1, ΔZ2, and ΔZ3, the alga and the mutants were cultured under light intensity conditions of 200 μmol photons/$m^2$ s in a state where 5% CO2 bubbles were supplied in an HS medium which is a minimum photosynthesis medium [see Table 1]. The number of initially inoculated cells was $1\times10^6$ cells/ml, and a growth curve was drawn by measuring the number of cells at intervals of 12 hours for 60 hours. FIG. 12 is an experimental result of comparing the cell growth rates through photosynthesis using carbon dioxide in the wild-type (WT) and the ZEP knock-out mutants. As illustrated in FIG. 12, it was confirmed that the mutants ΔZ1, ΔZ2, and ΔZ3 had a growth rate at a level similar to the wild-type as the culture period elapsed.

Example 5: Identification of Pigment Production

The contents of lutein and zeaxanthin pigments of the cells were quantitatively analyzed at intervals of 12 hours by using HPLC simultaneously while carrying out the experiment in FIG. 12. Through FIG. 13, the amounts of lutein and zeaxanthin produced from the *Chlamydomonas reinhardtii* cw15 wild-type (WT) and the ZEP knock-out mutants over time were compared with one another. When the results of the ZEP knock-out mutants were compared to those of the wild-type, it could be confirmed that the amounts of lutein produced from the ZEP knock-out mutants were at a level similar to that of the wild-type, but the amounts of zeaxanthin insignificantly present in the wild-type were greatly increased by at least 50 times or more.

The following Table 3 and FIG. 14 compare the contents of zeaxanthin and lutein from higher plants known to have high contents of zeaxanthin and lutein with those from the *Chlamydomonas reinhardtii* cw15 wild-type (WT) and the ZEP knock-out mutants. For the *Chlamydomonas*, the content (μg/100 g) was calculated by dividing the amounts of lutein and zeaxanthin pigments by the dry weight of the cells at 36 hours in FIG. 12. The pigment contents (μg/100 g) of the remaining higher plants known to have high contents of zeaxanthin and lutein were compared by citing the USDA National Nutrient Database for Standard Reference, Release 23 (2010). When the contents of lutein and zeaxanthin were compared with those of the higher plants, the *Chlamydomonas reinhardtii* wild-type exhibited a content which is higher by at least 6 times or more (than that of nasturtium) and the ZEP gene knock-out mutants exhibited a content which is higher by 12 times or more (than that of nasturtium). In particular, when the content of zeaxanthin was compared with those of the higher plants, the ZEP gene knock-out mutants exhibited a content which is higher by at least 120 times or more (than that of orange pepper).

Through FIGS. 13 and 14, high productivities and contents were identified, and through this, it could be confirmed that the mutants had high competitiveness in the raw material market of the lutein and zeaxanthin pigment industry.

TABLE 3

| Product | Lutein + Zeaxanthin (μg/100 g) |
| --- | --- |
| *Chlamydomonas*, cw15-, WT | 274,397 |
| *Chlamydomonas*, ZEP mutant 1 (ΔZ1) | 528,353 |
| *Chlamydomonas*, ZEP mutant 2 (ΔZ2) | 502,520 |
| *Chlamydomonas*, ZEP mutant 3 (ΔZ3) | 544,684 |
| *Nasturtium* (yellow flowers) | 45,000 |
| Kale (raw) | 39,550 |
| Kale (cooked) | 18,246 |
| Dandelion leaves (raw) | 13,610 |
| *Nasturtium* (leaves) | 13,600 |
| Turnip greens (raw) | 12,825 |
| Spinach (raw) | 12,198 |
| Spinach (cooked) | 11,308 |
| Swiss chard (raw or cooked) | 11,000 |
| Turnip greens (cooked) | 8440 |

TABLE 3-continued

| Product | Lutein + Zeaxanthin (μg/100 g) |
|---|---|
| Collard greens (cooked) | 7694 |
| Watercress (raw) | 5767 |
| Garden peas (raw) | 2593 |
| Romaine lettuce | 2312 |
| Zucchini | 2125 |
| Brussels sprouts | 1590 |
| Pistachio nuts | 1205 |
| Broccoli | 1121 |
| Carrot (cooked) | 687 |
| Maize/corn | 642 |
| Egg (hard boiled) | 353 |
| Avocado (raw) | 271 |
| Carrot (raw) | 256 |
| Kiwi fruit | 122 |

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

INFORMATION ON DEPOSIT OF MICROORGANISM

Name of Depository Institution: Korea Research Institute of Bioscience & Biotechnology Accession number: KCTC13230BP Commissioned date: Mar. 22, 2017

The invention claimed is:

1. A *Chlamydomonas reinhardtii* mutant having a ZEP gene mutation in which a base sequence represented by SEQ ID No. 2 is inserted between a 816th base and a 817th base in a ZEP gene sequence of a *Chlamydomonas reinhardtii* represented by SEQ ID No. 1 and having an ability to produce a xanthophyll.

2. The *Chlamydomonas reinhardtii* mutant of claim 1, wherein the *Chlamydomonas reinhardtii* mutant has a ZEP gene mutation represented by SEQ ID No. 3.

3. The *Chlamydomonas reinhardtii* mutant of claim 1, wherein the mutant has an ability to produce one or more pigments selected from a group consisting of lutein and zeaxanthin; and chlorophyll b, chlorophyll a, and β-carotene.

4. A composition for oral administration comprising one or more selected from a group consisting of a culture of the mutant of claim 1, a dry material thereof, and an extract thereof.

* * * * *

SEQUENCE LISTING

```
<160> NUMBER OF SEQ ID NOS: 26

<210> SEQ ID NO 1
<211> LENGTH: 6693
<212> TYPE: DNA
<213> ORGANISM: Chlamydomonas reinhardtii

<400> SEQUENCE: 1

gcgacgcacg gctgggccaa attcgccaac ggcaggagac caaatcgatc gaggcgatct     60

tgcgaagttc tcggacaaat cgatcgcacc catagtgatt taagcattac atttgcccaa    120

ggcgtgagaa gtgcgaggcc cgaacggcta tgacgccaat gcgcagctta cgacatttaa    180

agcaaattat tcatacatca tacagcacgc ttatgtgaag aaagccagga ttttaggctc    240

tcgccccgat caagacgatc tccccattgc gaagttctcg gtttctttcc ggttcgcctg    300

ctccgtatga tttacctttg cgctacaaca gcgacttaaa cgacctacgt cgccttactg    360

tgtgcgcgta cgtgtttgta gctgtgagat agttttgtcc gcagcgtacc cgcaaataga    420

atgctcgcga gcacttacac gccctgtggc gttcgccagg tggcaggccg cacggttgca    480

gtgcccagca gcttggtcgc gccagtggca gtcgctcggt cgctggggtt ggcgccctac    540

gtccctgtat gtgagccttc tgcggcgctt ccggcctgcc agcagcctag cgggcgtcgt    600

catgttcaga ctgctgccac tctccgtgcc gacaacccca gctcggtcgc gcagctggtg    660

catcagaatg gaaaggggat gaaggttatt atcgccggcg cgggcatcgg cggcctggtg    720

ctagccgttg cacttctgaa gcagggcttc caggttcagg tctttgagcg cgacctgacg    780

gccatccgcg gcgagggcaa gtaccgtgga cccatccagg tgcgttcgcc ggaacaccaa    840

cgcgcttgtt tttgctgtgc cgcgaccatg aactaggcct tatcttgagg tgttagcatg    900

tttagccagc gttggatctg tgtggcgagg ttggggtgag aacccttcct gtgtacctgc    960

tcgggcgtac cttgtgcccc accgctgact ggcttactta atgacaaaac gcaggttcaa   1020

agcaatgcgc tcgctgcgct ggaggctatc gatcccgagg tggccgcgga ggtgctgcgc   1080

gagggctgca tcactggcga ccgtatcaac gggctctgcg acggcctgac tggcgagtgg   1140

tgagtaggca atccagctgt gcatccagtc gcgcggttgc ggaggtcgtc tcgggaaacg   1200

cgacgtggcg tccactcgcc caaggagtgg tctcccgcag cgtggtctcc cgcagctcgg   1260

gtgcaacacc ctgccccctg ccgcgagcgc gctgcgcttg cttatgttgc gcagcggtgt   1320

gagttacaac agcttctgtt gaagagctgt catacgaagc acggcgcgct gtggcgctgc   1380
```

-continued

```
agccgtgctg tggaaactcc aacacctcca ccgccagcct gcgcacgcac acgcaataca   1440
ctcgcctcgt gtgccccctc ctcacacaac ggcatgtgac actcagtttt aactcttatt   1500
ttgacagctg agagctacac gcttgggtga atggggaggt ccttgatgtt tcgttgcact   1560
ccgtggctcc ggagtccgtg cggaccgtca cccacaaatg ggagcgcacg gctttcttgt   1620
gctgtctgcc ccgttagcca ctaactgcga atgaccttga cagtttactt tgctattttt   1680
ccttccaggt acgtcaagtt cgacacgttc cacccggcgg tcagcaaggg cctgccggtg   1740
acccgcgtca tcagccgcct cacgctgcag cagatcctgg ccaaagccgt ggagcggtga   1800
gccgtgcgcg cggtgtgatg gctttagcgt cagtgctagc atgggggttg gtgggtggta   1860
atcgcggcgc ccatggccgg gtagcagcgg ccgaaagctg gcgcagagcg cgcgttggac   1920
aagcggtcct gttgccggta tgggcacgag cagggcgctg gtgcgggcaa agggcagagt   1980
ggagttgcag agcagcgctg gcgtcggctg tgcgctctcc aaatggcctc gtggcattct   2040
gacgggacac atcctggaaa atagtagcgc acccaactgc tggtggctcc tcgtacaatc   2100
cccccaattt acaatcgctc gttctggctc gcagctacgg cggcccccggc accatccaga   2160
acggctgcaa cgtgaccgag ttcacggagc gccgcaacga caccaccggc aacaacgagg   2220
tgagagcgtg ctaagaagag catgcacgtg gagcgtgtaa aattgtgtgg cctgaagcgg   2280
cagtgcctgc ggcatggact aggtggttgc agcatgctgc gcgcgtgggt tgccggtcag   2340
gaaaccgccg gaccgagccg cgcagattca gtcaggagcg gattaggaag tttgaaaaac   2400
agggttcgga gtgtgcaagc gggctcagga gctgtggtgc ctttctacac cggtcgccct   2460
accaggcacc cactgaaact gtaaaaccgt tgctgcgccg gcgatgccct ctacttcact   2520
aggtgactgt gcagctggag gacgggcgca cgtttgcggc cgacgtgctg gtgggcgccg   2580
acggcatctg gtccaagatc cgtaagcagc tcattggcga gaccaaggcc aactacagcg   2640
ggtacacctg ctacaccggt gagattattg accttcaagt tggaaggagg gagcgggggg   2700
agcggaatgg aaggaagcag cgtggacggg gcgcacggag gggaggggac tgcgggtcat   2760
agcgccgcct tgcggggcgt gaggagtgtt gggcggatat tcagttttct ttgcccaaga   2820
tcttcccaca atccgcgtgt gtctgacgcg ggatgtggcc cctgctgcca tggcttcgca   2880
ggcatctcgg actttacgcc ggcggacatt gacattgtgg gctaccgcgt gttcctgggc   2940
aacggccagt actttgtcag cagcgacgtg ggcaacggca agatgcagtg gtgagcggcg   3000
gcgggcgggc gagcgagggc tgcggggtct ggagggtgtg taccgggcgg aagggagggg   3060
aagggagggg aagggaaggc aggatgcagg cgagggcagg atgtgatggt gggaagaggg   3120
cgtggcgagc agcaactgga aaggtggtgg gtaaaaaaat ggtccatgaa tatggctcgg   3180
tacagttcaa agcatggaaa tggaacccgc cgtctgctgc accatgggcg tgagcgggga   3240
gtacgcgact cctggacagc cgtaacaatg cggatggcct caacaagcca ggagcggcac   3300
gaacccagct cacgagcgca cagcgtgcca ggacggcggc cggcaaggat gaaatgtttt   3360
tcctaatata aatgcggact cctgacgcat tatatccatt ttgccactga gccaaagaca   3420
catatataca cgtgcgccgc cgtcctgcgc cacagccgcc tagcgctccg gccgcgcccg   3480
gttccctcgg cgtcatgcgc tggagccccc tcgcaccctg caccgcaaag cccatcaaca   3540
ccacactcgt ccccacaccg cgagtcaccg ccactgcact cgctgtccct caacccgtca   3600
caatctcgcc gacacgcgat aacgaaccca cgcaggtacg gcttccacaa ggagccgtct   3660
ggcggcaccg accccgaggg cagccgcaag gcgcgcctgc tgcagatctt tggccactgg   3720
```

-continued aacgacaacg tggtggacct gatcaaggcc acgcccgagg aggacgtgct gcgccgcgac 3780
atctttgaca ggtacggaaa aagggagagc ggggtggctg gagggcggga aagggcgaag 3840
gggcggagaa agaaatgact aggggatggt gttcatttgt gggattgaga ggggtccgcg 3900
gatcccggca gagggcgcca gtggcaaggc gtgggagtcg cggggcggac aatgctgggc 3960
caggggcgcc tagtcacccc gggacactgt ctcagtatgc cgccgtcccg gccgcgccgc 4020
acaggccgcc catcttcacc tggagcaagg gccgcgtggc cctgctgggc gacagcgcgc 4080
acgccatgca gcccaacctg ggccagggcg gctgcatggc cattgaggac gcctacgagc 4140
tggccatcga cctcagccgc gccgtgtccg acaaggccgg aaacgcggcg gcggtggacg 4200
tggagggcgt gctgcgcagc taccaggaca gccgcatttt gcgcgtcagc gccattcacg 4260
gcatggcggg tgagagctgc aaccagcgta gtcgggctgg gctgctgtgg gcagggtcgg 4320
gttgggttgg gcgcacgtgg gcggcgagtg tatgtgcagt gtgacgtgca cactatcata 4380
atactttatg ctcaccgcac cgcgccgcgc cgcaccacgc gccacaggca tggctgcctt 4440
catggccagc acctacaagt gctacctggg cgagggctgg agcaagtggg ttgaggggct 4500
gcgcatcccg caccccggcc gcgtggtggg gcggctggtg atgctgctca ccatgcccag 4560
cgtgctggag tgggtgctgg gcggcaacac cgaccacgtg gcgccgcacc gcaccagcta 4620
ctgctcgctg ggcgacaagc ccaaggtgag cggctgccgg gctggggggg ggtggaggga 4680
gaggaggagg attgcgggga gacgagggag ggcaaggcag gcgctgcctt cgtggatgca 4740
ccgccccgtc gttagcagga cctcaggaac tcgtccccaa aaccacaaca gaacccccaa 4800
tatcgcctct tccttcactg cttgtcacgc ctggtccgcc gaccgcaggc tttccccgag 4860
agccgcttcc ccgagttcat gaacaacgac gcctccatca tccgctcctc ccacgccgac 4920
tggctgctgg tggcggagcg cgacgccgcc acggccgccg ccgccaacgt gaacgccgcc 4980
accggcagca gcgccgccgc ggccgccgcc gccgacgtga acagcagctg ccagtgcaag 5040
ggcatctaca tggcggactc ggcggccctg gtgggccgct gcggcgccac ctcgcgcccc 5100
gcgctggccg tggacgacgt gcacgtcgcc gagagtcacg cgcaggtctg gcgcggcctc 5160
gccggcctcc ccccctcctc gtcgtccgcc tccaccgccg ccgcctctgc gtccgccgcc 5220
tcctctgccg ccagcggcac cgccagcacc ctgggcagct cggagggcta ctggctccgc 5280
gacctgggca gcggccgcgg cacctgggtc aacggcaagc gcctgcccga cggcgccacg 5340
gtgcagctgt ggcccggcga cgcggtggag ttcggccggc accccagcca cgaggtgttc 5400
aaggtgaaga tgcagcacgt gacgctgcgc agcgacgagc tcagcggcca ggcctacacc 5460
acgctcatgg tgggcaagat ccggaacaac gactacgtca tgcccgagtc gcggccggac 5520
ggcggcagcc agcagccggg ccgcctggtg acggcttaag cggcgccgtg cgtaagggcc 5580
ggcttacggg ggcggcagtg tcgctgtgga gggatggtct ggggtgggag gaatgggagg 5640
agagcggcgg gagcccgagg agcggagcgc tggaggcttg cggagcggca gcttgggaag 5700
agctgcggag agaggaagga gcgcagggcg cttggagcac gcgccagatt acgatcacgg 5760
cagcgcgagg cgcgcgtctg acttcgaagt ggtaaggaag atttcatgta tgattgcgtc 5820
gagggacacc gcaagtttta cgcgcggcgg agggagcctt ggggcataca acagtacgag 5880
cgggcgttgg tgagaaggtg gtcactccgt atgagaagat ggttactccg taccttcgtg 5940
agaagctgct gcgcacaagt tacgaaccta tctgtgtgga gagcccggta gtatatcagg 6000
ggcgagggtc atgaacgcga gtggcgagtc tgtgagcgcc aatttgttat gcggcataat 6060
ttcgcatcgg ggtattacgt ctacaaaatg ttgagctggc ttagcgcagg aggcaacacc 6120

-continued tcaggcagaa tgtacgaatg tgtgcagaag ggcagagtca aggcagaggc ggagaagttg 6180
tcagggctgt gtgtggtttg gtcagggcgt ggctagatgg atatgagacc cgccgccgtc 6240
tccagattgt ggcggaggtg gaactctcgg cccccgcgcc agtccccgcg gccagcgcat 6300
cccgccatgc gggttgttgg ctggtgcatc gcgcggggtg tgctatgagt gtggaaacac 6360
tatgtcgcgt gtcgtgctga ggtctgttga gaggtttcgt cgtttgtgca tgtcctgtcc 6420
cggttggagt ttgagcgagg tggttcaaag tttttggatc gcgtgggaga gactgaaacg 6480
gtttggtgag aatggttgag acagaggttg ggcttggaaa ctggaggaga ggagcagcgt 6540
aactcgagga cgatgcagta gatgcaccac aacagttgtg gtgggcgcct ggagtaacac 6600
gcgtgccacc aacacgcaat tacagagatc cgtcatacag gagggatcat atgcgattta 6660
attttggttt tgcatttgta agacgttttc aca 6693

<210> SEQ ID NO 2
<211> LENGTH: 42
<212> TYPE: DNA
<213> ORGANISM: Artificial Sequence
<220> FEATURE:
<223> OTHER INFORMATION: Chlamydomonas reinhardtii ZEP mutant 1-insert

<400> SEQUENCE: 2
gaaattaata agactcatta tattccggcg aacgcacctg ga 42

<210> SEQ ID NO 3
<211> LENGTH: 6735
<212> TYPE: DNA
<213> ORGANISM: Artificial Sequence
<220> FEATURE:
<223> OTHER INFORMATION: Synthetic sequence, ZEP mutant 1

<400> SEQUENCE: 3
gcgacgcacg gctgggccaa attcgccaac ggcaggagac caaatcgatc gaggcgatct 60
tgcgaagttc tcggacaaat cgatcgcacc catagtgatt taagcattac atttgcccaa 120
ggcgtgagaa gtgcgaggcc cgaacggcta tgacgccaat gcgcagctta cgacatttaa 180
agcaaattat tcatacatca tacagcacgc ttatgtgaag aaagccagga ttttaggctc 240
tcgccccgat caagacgatc tccccattgc gaagttctcg gtttctttcc ggttcgcctg 300
ctccgtatga tttacctttg cgctacaaca gcgacttaaa cgacctacgt cgccttactg 360
tgtgcgcgta cgtgtttgta gctgtgagat agttttgtcc gcagcgtacc cgcaaataga 420
atgctcgcga gcacttacac gccctgtggc gttcgccagg tggcaggccg cacggttgca 480
gtgcccagca gcttggtcgc gccagtggca gtcgctcggt cgctggggtt ggcgccctac 540
gtccctgtat gtgagccttc tgcggcgctt ccggcctgcc agcagcctag cgggcgtcgt 600
catgttcaga ctgctgccac tctccgtgcc gacaacccca gctcggtcgc gcagctggtg 660
catcagaatg gaaaggggat gaaggttatt atcgccggcg cgggcatcgg cggcctggtg 720
ctagccgttg cacttctgaa gcagggcttc caggttcagg tctttgagcg cgacctgacg 780
gccatccgcg gcgagggcaa gtaccgtgga cccatcgaaa ttaataagac tcattatatt 840
ccggcgaacg cacctggaca ggtgcgttcg ccggaacacc aacgcgcttg tttttgctgt 900
gccgcgacca tgaactaggc cttatcttga ggtgttagca tgtttagcca gcgttggatc 960
tgtgtggcga ggttggggtg agaacccttc ctgtgtacct gctcgggcgt accttgtgcc 1020
ccaccgctga ctggcttact taatgacaaa acgcaggttc aaagcaatgc gctcgctgcg 1080

-continued

```
ctggaggcta tcgatcccga ggtggccgcg gaggtgctgc gcgagggctg catcactggc   1140
gaccgtatca acgggctctg cgacggcctg actggcgagt ggtgagtagg caatccagct   1200
gtgcatccag tcgcgcggtt gcggaggtcg tctcgggaaa cgcgacgtgg cgtccactcg   1260
cccaaggagt ggtctcccgc agcgtggtct cccgcagctc gggtgcaaca ccctgccccc   1320
tgccgcgagc gcgctgcgct tgcttatgtt gcgcagcggt gtgagttaca acagcttctg   1380
ttgaagagct gtcatacgaa gcacggcgcg ctgtggcgct gcagccgtgc tgtggaaact   1440
ccaacacctc caccgccagc ctgcgcacgc acacgcaata cactcgcctc gtgtgccccc   1500
tcctcacaca acggcatgtg acactcagtt ttaactctta ttttgacagc tgagagctac   1560
acgcttgggt gaatggggag gtccttgatg tttcgttgca ctccgtggct ccggagtccg   1620
tgcggaccgt cacccacaaa tgggagcgca cggctttctt gtgctgtctg ccccgttagc   1680
cactaactgc gaatgacctt gacagtttac tttgctattt ttccttccag gtacgtcaag   1740
ttcgacacgt tccacccggc ggtcagcaag ggcctgccgg tgacccgcgt catcagccgc   1800
ctcacgctgc agcagatcct ggccaaagcc gtggagcggt gagccgtgcg cgcggtgtga   1860
tggctttagc gtcagtgcta gcatgggggt tggtgggtgg taatcgcggc gcccatggcc   1920
gggtagcagc ggccgaaagc tggcgcagag cgcgcgttgg acaagcggtc ctgttgccgg   1980
tatgggcacg agcagggcgc tggtgcgggc aaagggcaga gtggagttgc agagcagcgc   2040
tggcgtcggc tgtgcgctct ccaaatggcc tcgtggcatt ctgacgggac acatcctgga   2100
aaatagtagc gcacccaact gctggtggct cctcgtacaa tccccccaat ttacaatcgc   2160
tcgttctggc tcgcagctac ggcggccccg gcaccatcca gaacggctgc aacgtgaccg   2220
agttcacgga gcgccgcaac gacaccaccg gcaacaacga ggtgagagcg tgctaagaag   2280
agcatgcacg tggagcgtgt aaaattgtgt ggcctgaagc ggcagtgcct gcggcatgga   2340
ctaggtggtt gcagcatgct gcgcgcgtgg gttgccggtc aggaaaccgc cggaccgagc   2400
cgcgcagatt cagtcaggag cggattagga agtttgaaaa acagggttcg gagtgtgcaa   2460
gcgggctcag gagctgtggt gcctttctac accggtcgcc ctaccaggca cccactgaaa   2520
ctgtaaaacc gttgctgcgc cggcgatgcc ctctacttca ctaggtgact gtgcagctgg   2580
aggacgggcg cacgtttgcg gccgacgtgc tggtgggcgc cgacggcatc tggtccaaga   2640
tccgtaagca gctcattggc gagaccaagg ccaactacag cggtgtacacc tgctacaccg   2700
gtgagattat tgaccttcaa gttggaagga gggagcgggg ggagcggaat ggaaggaagc   2760
agcgtggacg gggcgcacgg aggggagggg actgcgggtc atagcgccgc cttgcggggc   2820
gtgaggagtg ttgggcggat attcagtttt ctttgcccaa gatcttccca caatccgcgt   2880
gtgtctgacg cgggatgtgg cccctgctgc catggcttcg caggcatctc ggactttacg   2940
ccggcggaca ttgacattgt gggctaccgc gtgttcctgg gcaacggcca gtactttgtc   3000
agcagcgacg tgggcaacgg caagatgcag tggtgagcgg cggcgggcgg gcgagcgagg   3060
gctgcggggt ctggagggtg tgtaccgggc ggaagggagg ggaagggagg ggaagggaag   3120
gcaggatgca ggcgagggca ggatgtgatg gtgggaagag ggcgtggcga gcagcaactg   3180
gaaaggtggt gggtaaaaaa atggtccatg aatatggctc ggtacagttc aaagcatgga   3240
aatggaaccc gccgtctgct gcaccatggg cgtgagcggg gagtacgcga ctcctggaca   3300
gccgtaacaa tgcggatggc ctcaacaagc caggagcggc acgaacccag ctcacgagcg   3360
cacagcgtgc caggacggcg gccggcaagg atgaaatgtt tttcctaata taaatgcgga   3420
ctcctgacgc attatatcca ttttgccact gagccaaaga cacatatata cacgtgcgcc   3480
```

-continued gccgtcctgc gccacagccg cctagcgctc cggccgcgcc cggttccctc ggcgtcatgc 3540
gctggagccc cctcgcaccc tgcaccgcaa agcccatcaa caccacactc gtccccacac 3600
cgcgagtcac cgccactgca ctcgctgtcc ctcaacccgt cacaatctcg ccgacacgcg 3660
ataacgaacc cacgcaggta cggcttccac aaggagccgt ctggcggcac cgaccccgag 3720
ggcagccgca aggcgcgcct gctgcagatc tttggccact ggaacgacaa cgtggtggac 3780
ctgatcaagg ccacgcccga ggaggacgtg ctgcgccgcg acatctttga caggtacgga 3840
aaaagggaga gcggggtggc tggagggcgg gaaagggcga aggggcggag aaagaaatga 3900
ctaggggatg gtgttcattt gtgggattga gaggggtccg cggatcccgg cagagggcgc 3960
cagtggcaag gcgtgggagt cgcggggcgg acaatgctgg gccaggggcg cctagtcacc 4020
ccgggacact gtctcagtat gccgccgtcc cggccgcgcc gcacaggccg cccatcttca 4080
cctggagcaa gggccgcgtg gccctgctgg gcgacagcgc gcacgccatg cagcccaacc 4140
tgggccaggg cggctgcatg gccattgagg acgcctacga gctggccatc gacctcagcc 4200
gcgccgtgtc cgacaaggcc ggaaacgcgg cggcggtgga cgtggagggc gtgctgcgca 4260
gctaccagga cagccgcatt ttgcgcgtca gcgccattca cggcatggcg ggtgagagct 4320
gcaaccagcg tagtcgggct gggctgctgt gggcagggtc gggttgggtt gggcgcacgt 4380
gggcggcgag tgtatgtgca gtgtgacgtg cacactatca taatacttta tgctcaccgc 4440
accgcgccgc gccgcaccac gcgccacagg catggctgcc ttcatggcca gcacctacaa 4500
gtgctacctg ggcgagggct ggagcaagtg ggttgagggg ctgcgcatcc cgcaccccgg 4560
ccgcgtggtg gggcggctgg tgatgctgct caccatgccc agcgtgctgg agtgggtgct 4620
gggcggcaac accgaccacg tggcgccgca ccgcaccagc tactgctcgc tgggcgacaa 4680
gcccaaggtg agcggctgcc gggctggggg ggggtggagg gagaggagga ggattgcggg 4740
gagacgaggg agggcaaggc aggcgctgcc ttcgtggatg caccgccccg tcgttagcag 4800
gacctcagga actcgtcccc aaaaccacaa cagaaccccc aatatcgcct cttccttcac 4860
tgcttgtcac gcctggtccg ccgaccgcag gctttccccg agagccgctt ccccgagttc 4920
atgaacaacg acgcctccat catccgctcc tcccacgccg actggctgct ggtggcggag 4980
cgcgacgccg ccacggccgc cgccgccaac gtgaacgccg ccaccggcag cagcgccgcc 5040
gcggccgccg ccgccgacgt gaacagcagc tgccagtgca agggcatcta catggcggac 5100
tcggcggccc tggtgggccg ctgcggcgcc acctcgcgcc ccgcgctggc cgtggacgac 5160
gtgcacgtcg ccgagagtca cgcgcaggtc tggcgcggcc tcgccggcct cccccccctcc 5220
tcgtcgtccg cctccaccgc cgccgcctct gcgtccgccg cctcctctgc cgccagcggc 5280
accgccagca ccctgggcag ctcggagggc tactggctcc gcgacctggg cagcggccgc 5340
ggcacctggg tcaacggcaa gcgcctgccc gacggcgcca cggtgcagct gtggcccggc 5400
gacgcggtgg agttcggccg gcaccccagc cacgaggtgt tcaaggtgaa gatgcagcac 5460
gtgacgctgc gcagcgacga gctcagcggc caggcctaca ccacgctcat ggtgggcaag 5520
atccggaaca acgactacgt catgcccgag tcgcggccgg acggcggcag ccagcagccg 5580
ggccgcctgg tgacggctta agcggcgccg tgcgtaaggg ccggcttacg ggggcggcag 5640
tgtcgctgtg gagggatggt ctggggtggg aggaatggga ggagagcggc gggagcccga 5700
ggagcggagc gctggaggct tgcggagcgg cagcttggga agagctgcgg agagaggaag 5760
gagcgcaggg cgcttggagc acgcgccaga ttacgatcac ggcagcgcga ggcgcgcgtc 5820

-continued

```
tgacttcgaa gtggtaagga agatttcatg tatgattgcg tcgagggaca ccgcaagttt   5880

tacgcgcggc ggagggagcc ttggggcata caacagtacg agcgggcgtt ggtgagaagg   5940

tggtcactcc gtatgagaag atggttactc cgtaccttcg tgagaagctg ctgcgcacaa   6000

gttacgaacc tatctgtgtg gagagcccgg tagtatatca ggggcgaggg tcatgaacgc   6060

gagtggcgag tctgtgagcg ccaatttgtt atgcggcata atttcgcatc ggggtattac   6120

gtctacaaaa tgttgagctg gcttagcgca ggaggcaaca cctcaggcag aatgtacgaa   6180

tgtgtgcaga agggcagagt caaggcagag gcggagaagt tgtcagggct gtgtgtggtt   6240

tggtcagggc gtggctagat ggatatgaga cccgccgccg tctccagatt gtggcggagg   6300

tggaactctc ggcccccgcg ccagtccccg cggccagcgc atcccgccat gcgggttgtt   6360

ggctggtgca tcgcgcgggg tgtgctatga gtgtggaaac actatgtcgc gtgtcgtgct   6420

gaggtctgtt gagaggtttc gtcgtttgtg catgtcctgt cccggttgga gtttgagcga   6480

ggtggttcaa agtttttgga tcgcgtggga gagactgaaa cggtttggtg agaatggttg   6540

agacagaggt tgggcttgga aactggagga gaggagcagc gtaactcgag gacgatgcag   6600

tagatgcacc acaacagttg tggtgggcgc ctggagtaac acgcgtgcca ccaacacgca   6660

attacagaga tccgtcatac aggagggatc atatgcgatt taattttggt tttgcatttg   6720

taagacgttt tcaca                                                    6735


<210> SEQ ID NO 4
<211> LENGTH: 44
<212> TYPE: DNA
<213> ORGANISM: Artificial Sequence
<220> FEATURE:
<223> OTHER INFORMATION: Chlamydomonas reinhardtii ZEP mutant 2-insert

<400> SEQUENCE: 4

tagctctaaa acatccaggt gcgttcgccg gactatagtg agta                      44


<210> SEQ ID NO 5
<211> LENGTH: 6737
<212> TYPE: DNA
<213> ORGANISM: Artificial Sequence
<220> FEATURE:
<223> OTHER INFORMATION: Synthetic sequence, ZEP mutant 2

<400> SEQUENCE: 5

gcgacgcacg gctgggccaa attcgccaac ggcaggagac caaatcgatc gaggcgatct     60

tgcgaagttc tcggacaaat cgatcgcacc catagtgatt taagcattac atttgcccaa    120

ggcgtgagaa gtgcgaggcc cgaacggcta tgacgccaat gcgcagctta cgacatttaa    180

agcaaattat tcatacatca tacagcacgc ttatgtgaag aaagccagga ttttaggctc    240

tcgccccgat caagacgatc tccccattgc gaagttctcg gtttctttcc ggttcgcctg    300

ctccgtatga tttacctttg cgctacaaca gcgacttaaa cgacctacgt cgccttactg    360

tgtgcgcgta cgtgtttgta gctgtgagat agttttgtcc gcagcgtacc cgcaaataga    420

atgctcgcga gcacttacac gccctgtggc gttcgccagg tggcaggccg cacggttgca    480

gtgcccagca gcttggtcgc gccagtggca gtcgctcggt cgctggggtt ggcgccctac    540

gtccctgtat gtgagccttc tgcggcgctt ccggcctgcc agcagcctag cgggcgtcgt    600

catgttcaga ctgctgccac tctccgtgcc gacaacccca gctcggtcgc gcagctggtg    660

catcagaatg gaaaggggat gaaggttatt atcgccggcg cgggcatcgg cggcctggtg    720

ctagccgttg cacttctgaa gcagggcttc caggttcagg tctttgagcg cgacctgacg    780
```

-continued

```
gccatccgcg gcgagggcaa gtaccgtgga cccatctagc tctaaaacat ccaggtgcgt    840
tcgccggact atagtgagta caggtgcgtt cgccggaaca ccaacgcgct tgtttttgct    900
gtgccgcgac catgaactag gccttatctt gaggtgttag catgtttagc cagcgttgga    960
tctgtgtggc gaggttgggg tgagaaccct tcctgtgtac ctgctcgggc gtaccttgtg   1020
ccccaccgct gactggctta cttaatgaca aaacgcaggt tcaaagcaat gcgctcgctg   1080
cgctggaggc tatcgatccc gaggtggccg cggaggtgct gcgcgagggc tgcatcactg   1140
gcgaccgtat caacgggctc tgcgacggcc tgactggcga gtggtgagta ggcaatccag   1200
ctgtgcatcc agtcgcgcgg ttgcggaggt cgtctcggga aacgcgacgt ggcgtccact   1260
cgcccaagga gtggtctccc gcagcgtggt ctcccgcagc tcgggtgcaa caccctgccc   1320
cctgccgcga gcgcgctgcg cttgcttatg ttgcgcagcg gtgtgagtta caacagcttc   1380
tgttgaagag ctgtcatacg aagcacggcg cgctgtggcg ctgcagccgt gctgtggaaa   1440
ctccaacacc tccaccgcca gcctgcgcac gcacacgcaa tacactcgcc tcgtgtgccc   1500
cctcctcaca caacggcatg tgacactcag ttttaactct tattttgaca gctgagagct   1560
acacgcttgg gtgaatgggg aggtccttga tgtttcgttg cactccgtgg ctccggagtc   1620
cgtgcggacc gtcacccaca aatgggagcg cacggctttc ttgtgctgtc tgccccgtta   1680
gccactaact gcgaatgacc ttgacagttt actttgctat tttccttcc aggtacgtca    1740
agttcgacac gttccacccg gcggtcagca agggcctgcc ggtgacccgc gtcatcagcc   1800
gcctcacgct gcagcagatc ctggccaaag ccgtggagcg gtgagccgtg cgcgcggtgt   1860
gatggcttta gcgtcagtgc tagcatgggg gttggtgggt ggtaatcgcg gcgcccatgg   1920
ccgggtagca gcggccgaaa gctggcgcag agcgcgcgtt ggacaagcgg tcctgttgcc   1980
ggtatgggca cgagcagggc gctggtgcgg gcaaagggca gagtggagtt gcagagcagc   2040
gctggcgtcg gctgtgcgct ctccaaatgg cctcgtggca ttctgacggg acacatcctg   2100
gaaaatagta gcgcacccaa ctgctggtgg ctcctcgtac aatcccccca atttacaatc   2160
gctcgttctg gctcgcagct acggcggccc cggcaccatc cagaacggct gcaacgtgac   2220
cgagttcacg gagcgccgca acgacaccac cggcaacaac gaggtgagag cgtgctaaga   2280
agagcatgca cgtggagcgt gtaaaattgt gtggcctgaa gcggcagtgc ctgcggcatg   2340
gactaggtgg ttgcagcatg ctgcgcgcgt gggttgccgg tcaggaaacc gccggaccga   2400
gccgcgcaga ttcagtcagg agcggattag gaagtttgaa aaacagggtt cggagtgtgc   2460
aagcgggctc aggagctgtg gtgcctttct acaccggtcg ccctaccagg cacccactga   2520
aactgtaaaa ccgttgctgc gccggcgatg ccctctactt cactaggtga ctgtgcagct   2580
ggaggacggg cgcacgtttg cggccgacgt gctggtgggc gccgacggca tctggtccaa   2640
gatccgtaag cagctcattg gcgagaccaa ggccaactac agcgggtaca cctgctacac   2700
cggtgagatt attgaccttc aagttggaag gagggagcgg ggggagcgga atggaaggaa   2760
gcagcgtgga cggggcgcac ggaggggagg ggactgcggg tcatagcgcc gccttgcggg   2820
gcgtgaggag tgttgggcgg atattcagtt ttctttgccc aagatcttcc cacaatccgc   2880
gtgtgtctga cgcgggatgt ggcccctgct gccatggctt cgcaggcatc tcggacttta   2940
cgccggcgga cattgacatt gtgggctacc gcgtgttcct gggcaacggc cagtactttg   3000
tcagcagcga cgtgggcaac ggcaagatgc agtggtgagc ggcggcgggc gggcgagcga   3060
gggctgcggg gtctggaggg tgtgtaccgg gcggaaggga ggggaaggga ggggaaggga   3120
```

-continued

```
aggcaggatg caggcgaggg caggatgtga tggtgggaag agggcgtggc gagcagcaac   3180
tggaaaggtg gtgggtaaaa aaatggtcca tgaatatggc tcggtacagt tcaaagcatg   3240
gaaatggaac ccgccgtctg ctgcaccatg ggcgtgagcg gggagtacgc gactcctgga   3300
cagccgtaac aatgcggatg gcctcaacaa gccaggagcg gcacgaaccc agctcacgag   3360
cgcacagcgt gccaggacgg cggccggcaa ggatgaaatg tttttcctaa tataaatgcg   3420
gactcctgac gcattatatc cattttgcca ctgagccaaa gacacatata tacacgtgcg   3480
ccgccgtcct gcgccacagc cgcctagcgc tccggccgcg cccggttccc tcggcgtcat   3540
gcgctggagc cccctcgcac cctgcaccgc aaagcccatc aacaccacac tcgtccccac   3600
accgcgagtc accgccactg cactcgctgt ccctcaaccc gtcacaatct cgccgacacg   3660
cgataacgaa cccacgcagg tacggcttcc acaaggagcc gtctggcggc accgaccccg   3720
agggcagccg caaggcgcgc ctgctgcaga tctttggcca ctggaacgac aacgtggtgg   3780
acctgatcaa ggccacgccc gaggaggacg tgctgcgccg cgacatcttt gacaggtacg   3840
gaaaaaggga gagcggggtg gctggagggc gggaaagggc gaaggggcgg agaaagaaat   3900
gactagggga tggtgttcat ttgtgggatt gagaggggtc cgcggatccc ggcagagggc   3960
gccagtggca aggcgtggga gtcgcggggc ggacaatgct gggccagggg cgcctagtca   4020
ccccgggaca ctgtctcagt atgccgccgt cccggccgcg ccgcacaggc cgcccatctt   4080
cacctggagc aagggccgcg tggccctgct gggcgacagc gcgcacgcca tgcagcccaa   4140
cctgggccag ggcggctgca tggccattga ggacgcctac gagctggcca tcgacctcag   4200
ccgcgccgtg tccgacaagg ccggaaacgc ggcggcggtg gacgtggagg gcgtgctgcg   4260
cagctaccag gacagccgca ttttgcgcgt cagcgccatt cacggcatgg cgggtgagag   4320
ctgcaaccag cgtagtcggg ctgggctgct gtgggcaggg tcgggttggg ttgggcgcac   4380
gtgggcggcg agtgtatgtg cagtgtgacg tgcacactat cataatactt tatgctcacc   4440
gcaccgcgcc gcgccgcacc acgcgccaca ggcatggctg ccttcatggc cagcacctac   4500
aagtgctacc tgggcgaggg ctggagcaag tgggttgagg ggctgcgcat cccgcacccc   4560
ggccgcgtgg tggggcggct ggtgatgctg ctcaccatgc ccagcgtgct ggagtgggtg   4620
ctgggcggca acaccgacca cgtggcgccg caccgcacca gctactgctc gctgggcgac   4680
aagcccaagg tgagcggctg ccgggctggg ggggggtgga gggagaggag gaggattgcg   4740
gggagacgag ggagggcaag gcaggcgctg ccttcgtgga tgcaccgccc cgtcgttagc   4800
aggacctcag gaactcgtcc ccaaaaccac aacagaaccc ccaatatcgc ctcttccttc   4860
actgcttgtc acgcctggtc cgccgaccgc aggctttccc cgagagccgc ttccccgagt   4920
tcatgaacaa cgacgcctcc atcatccgct cctcccacgc cgactggctg ctggtggcgg   4980
agcgcgacgc cgccacggcc gccgccgcca acgtgaacgc cgccaccggc agcagcgccg   5040
ccgcggccgc cgccgccgac gtgaacagca gctgccagtg caagggcatc tacatggcgg   5100
actcggcggc cctggtgggc cgctgcggcg ccacctcgcg ccccgcgctg gccgtggacg   5160
acgtgcacgt cgccgagagt cacgcgcagg tctggcgcgg cctcgccggc ctccccccct   5220
cctcgtcgtc cgcctccacc gccgccgcct ctgcgtccgc cgcctcctct gccgccagcg   5280
gcaccgccag caccctgggc agctcggagg gctactggct ccgcgacctg ggcagcggcc   5340
gcggcacctg ggtcaacggc aagcgcctgc ccgacggcgc cacggtgcag ctgtggcccg   5400
gcgacgcggt ggagttcggc cggcacccca gccacgaggt gttcaaggtg aagatgcagc   5460
acgtgacgct gcgcagcgac gagctcagcg gccaggccta caccacgctc atggtgggca   5520
```

```
agatccggaa caacgactac gtcatgcccg agtcgcggcc ggacggcggc agccagcagc   5580
cgggccgcct ggtgacggct taagcggcgc cgtgcgtaag ggccggctta cgggggcggc   5640
agtgtcgctg tggagggatg gtctggggtg ggaggaatgg gaggagagcg gcgggagccc   5700
gaggagcgga gcgctggagg cttgcggagc ggcagcttgg gaagagctgc ggagagagga   5760
aggagcgcag ggcgcttgga gcacgcgcca gattacgatc acggcagcgc gaggcgcgcg   5820
tctgacttcg aagtggtaag gaagatttca tgtatgattg cgtcgaggga caccgcaagt   5880
tttacgcgcg gcggagggag ccttggggca tacaacagta cgagcgggcg ttggtgagaa   5940
ggtggtcact ccgtatgaga agatggttac tccgtacctt cgtgagaagc tgctgcgcac   6000
aagttacgaa cctatctgtg tggagagccc ggtagtatat caggggcgag ggtcatgaac   6060
gcgagtggcg agtctgtgag cgccaatttg ttatgcggca taatttcgca tcggggtatt   6120
acgtctacaa aatgttgagc tggcttagcg caggaggcaa cacctcaggc agaatgtacg   6180
aatgtgtgca gaagggcaga gtcaaggcag aggcggagaa gttgtcaggg ctgtgtgtgg   6240
tttggtcagg gcgtggctag atggatatga gacccgccgc cgtctccaga ttgtggcgga   6300
ggtggaactc tcggcccccg cgccagtccc cgcggccagc gcatcccgcc atgcgggttg   6360
ttggctggtg catcgcgcgg ggtgtgctat gagtgtggaa acactatgtc gcgtgtcgtg   6420
ctgaggtctg ttgagaggtt tcgtcgtttg tgcatgtcct gtcccggttg gagtttgagc   6480
gaggtggttc aaagtttttg gatcgcgtgg gagagactga aacggtttgg tgagaatggt   6540
tgagacagag gttgggcttg gaaactggag gagaggagca gcgtaactcg aggacgatgc   6600
agtagatgca ccacaacagt tgtggtgggc gcctggagta acacgcgtgc caccaacacg   6660
caattacaga gatccgtcat acaggaggga tcatatgcga tttaattttg gttttgcatt   6720
tgtaagacgt tttcaca                                                  6737
```

<210> SEQ ID NO 6
<211> LENGTH: 6694
<212> TYPE: DNA
<213> ORGANISM: Artificial Sequence
<220> FEATURE:
<223> OTHER INFORMATION: Synthetic sequence, ZEP mutant 3

<400> SEQUENCE: 6

```
gcgacgcacg gctgggccaa attcgccaac ggcaggagac caaatcgatc gaggcgatct     60
tgcgaagttc tcggacaaat cgatcgcacc catagtgatt taagcattac atttgcccaa    120
ggcgtgagaa gtgcgaggcc cgaacggcta tgacgccaat gcgcagctta cgacatttaa    180
agcaaattat tcatacatca tacagcacgc ttatgtgaag aaagccagga ttttaggctc    240
tcgccccgat caagacgatc tccccattgc gaagttctcg gtttctttcc ggttcgcctg    300
ctccgtatga tttacctttg cgctacaaca gcgacttaaa cgacctacgt cgccttactg    360
tgtgcgcgta cgtgtttgta gctgtgagat agttttgtcc gcagcgtacc cgcaaataga    420
atgctcgcga gcacttacac gccctgtggc gttcgccagg tggcaggccg cacggttgca    480
gtgcccagca gcttggtcgc gccagtggca gtcgctcggt cgctggggtt ggcgccctac    540
gtccctgtat gtgagccttc tgcggcgctt ccggcctgcc agcagcctag cgggcgtcgt    600
catgttcaga ctgctgccac tctccgtgcc gacaacccca gctcggtcgc gcagctggtg    660
catcagaatg gaaaggggat gaaggttatt atcgccggcg cgggcatcgg cggcctggtg    720
ctagccgttg cacttctgaa gcagggcttc caggttcagg tctttgagcg cgacctgacg    780
```

-continued

```
gccatccgcg gcgagggcaa gtaccgtgga cccatcacag gtgcgttcgc cggaacacca    840
acgcgcttgt ttttgctgtg ccgcgaccat gaactaggcc ttatcttgag gtgttagcat    900
gtttagccag cgttggatct gtgtggcgag gttggggtga gaacccttcc tgtgtacctg    960
ctcgggcgta ccttgtgccc caccgctgac tggcttactt aatgacaaaa cgcaggttca   1020
aagcaatgcg ctcgctgcgc tggaggctat cgatcccgag gtggccgcgg aggtgctgcg   1080
cgagggctgc atcactggcg accgtatcaa cgggctctgc gacggcctga ctggcgagtg   1140
gtgagtaggc aatccagctg tgcatccagt cgcgcggttg cggaggtcgt ctcgggaaac   1200
gcgacgtggc gtccactcgc ccaaggagtg gtctcccgca gcgtggtctc ccgcagctcg   1260
ggtgcaacac cctgccccct gccgcgagcg cgctgcgctt gcttatgttg cgcagcggtg   1320
tgagttacaa cagcttctgt tgaagagctg tcatacgaag cacggcgcgc tgtggcgctg   1380
cagccgtgct gtggaaactc caacacctcc accgccagcc tgcgcacgca cacgcaatac   1440
actcgcctcg tgtgccccct cctcacacaa cggcatgtga cactcagttt taactcttat   1500
tttgacagct gagagctaca cgcttgggtg aatggggagg tccttgatgt ttcgttgcac   1560
tccgtggctc cggagtccgt gcggaccgtc acccacaaat gggagcgcac ggctttcttg   1620
tgctgtctgc cccgttagcc actaactgcg aatgaccttg acagtttact ttgctatttt   1680
tccttccagg tacgtcaagt tcgacacgtt ccacccggcg gtcagcaagg gcctgccggt   1740
gacccgcgtc atcagccgcc tcacgctgca gcagatcctg gccaaagccg tggagcggtg   1800
agccgtgcgc gcggtgtgat ggctttagcg tcagtgctag catgggggtt ggtgggtggt   1860
aatcgcggcg cccatggccg ggtagcagcg gccgaaagct ggcgcagagc gcgcgttgga   1920
caagcggtcc tgttgccggt atgggcacga gcagggcgct ggtgcgggca aagggcagag   1980
tggagttgca gagcagcgct ggcgtcggct gtgcgctctc caaatggcct cgtggcattc   2040
tgacgggaca catcctggaa aatagtagcg cacccaactg ctggtggctc ctcgtacaat   2100
ccccccaatt tacaatcgct cgttctggct cgcagctacg gcggccccgg caccatccag   2160
aacggctgca acgtgaccga gttcacggag cgccgcaacg acaccaccgg caacaacgag   2220
gtgagagcgt gctaagaaga gcatgcacgt ggagcgtgta aaattgtgtg gcctgaagcg   2280
gcagtgcctg cggcatggac taggtggttg cagcatgctg cgcgcgtggg ttgccggtca   2340
ggaaaccgcc ggaccgagcc gcgcagattc agtcaggagc ggattaggaa gtttgaaaaa   2400
cagggttcgg agtgtgcaag cgggctcagg agctgtggtg cctttctaca ccggtcgccc   2460
taccaggcac ccactgaaac tgtaaaaccg ttgctgcgcc ggcgatgccc tctacttcac   2520
taggtgactg tgcagctgga ggacgggcgc acgtttgcgg ccgacgtgct ggtgggcgcc   2580
gacggcatct ggtccaagat ccgtaagcag ctcattggcg agaccaaggc caactacagc   2640
gggtacacct gctacaccgg tgagattatt gaccttcaag ttggaaggag ggagcggggg   2700
gagcggaatg gaaggaagca gcgtggacgg ggcgcacgga ggggagggga ctgcgggtca   2760
tagcgccgcc ttgcggggcg tgaggagtgt tgggcggata ttcagttttc tttgcccaag   2820
atcttcccac aatccgcgtg tgtctgacgc gggatgtggc ccctgctgcc atggcttcgc   2880
aggcatctcg gactttacgc cggcggacat tgacattgtg ggctaccgcg tgttcctggg   2940
caacggccag tactttgtca gcagcgacgt gggcaacggc aagatgcagt ggtgagcggc   3000
ggcgggcggg cgagcgaggg ctgcggggtc tggagggtgt gtaccgggcg gaagggaggg   3060
gaagggaggg gaagggaagg caggatgcag gcgagggcag gatgtgatgg tgggaagagg   3120
gcgtggcgag cagcaactgg aaaggtggtg ggtaaaaaaa tggtccatga atatggctcg   3180
```

```
gtacagttca aagcatggaa atggaacccg ccgtctgctg caccatgggc gtgagcgggg   3240

agtacgcgac tcctggacag ccgtaacaat gcggatggcc tcaacaagcc aggagcggca   3300

cgaacccagc tcacgagcgc acagcgtgcc aggacggcgg ccggcaagga tgaaatgttt   3360

ttcctaatat aaatgcggac tcctgacgca ttatatccat tttgccactg agccaaagac   3420

acatatatac acgtgcgccg ccgtcctgcg ccacagccgc ctagcgctcc ggccgcgccc   3480

ggttccctcg gcgtcatgcg ctggagcccc ctcgcaccct gcaccgcaaa gcccatcaac   3540

accacactcg tccccacacc gcgagtcacc gccactgcac tcgctgtccc tcaacccgtc   3600

acaatctcgc cgacacgcga taacgaaccc acgcaggtac ggcttccaca aggagccgtc   3660

tggcggcacc gaccccgagg gcagccgcaa ggcgcgcctg ctgcagatct ttggccactg   3720

gaacgacaac gtggtggacc tgatcaaggc cacgcccgag gaggacgtgc tgcgccgcga   3780

catctttgac aggtacggaa aaagggagag cggggtggct ggagggcggg aaagggcgaa   3840

ggggcggaga aagaaatgac taggggatgg tgttcatttg tgggattgag aggggtccgc   3900

ggatcccggc agagggcgcc agtggcaagg cgtgggagtc gcggggcgga caatgctggg   3960

ccaggggcgc ctagtcaccc cgggacactg tctcagtatg ccgccgtccc ggccgcgccg   4020

cacaggccgc ccatcttcac ctggagcaag ggccgcgtgg ccctgctggg cgacagcgcg   4080

cacgccatgc agcccaacct gggccagggc ggctgcatgg ccattgagga cgcctacgag   4140

ctggccatcg acctcagccg cgccgtgtcc gacaaggccg gaaacgcggc ggcggtggac   4200

gtggagggcg tgctgcgcag ctaccaggac agccgcattt tgcgcgtcag cgccattcac   4260

ggcatggcgg gtgagagctg caaccagcgt agtcgggctg ggctgctgtg ggcagggtcg   4320

ggttgggttg ggcgcacgtg ggcggcgagt gtatgtgcag tgtgacgtgc acactatcat   4380

aatactttat gctcaccgca ccgcgccgcg ccgcaccacg cgccacaggc atggctgcct   4440

tcatggccag cacctacaag tgctacctgg gcgagggctg gagcaagtgg gttgaggggc   4500

tgcgcatccc gcaccccggc cgcgtggtgg ggcggctggt gatgctgctc accatgccca   4560

gcgtgctgga gtgggtgctg ggcggcaaca ccgaccacgt ggcgccgcac cgcaccagct   4620

actgctcgct gggcgacaag cccaaggtga gcggctgccg ggctgggggg gggtggaggg   4680

agaggaggag gattgcgggg agacgaggga gggcaaggca ggcgctgcct tcgtggatgc   4740

accgccccgt cgttagcagg acctcaggaa ctcgtcccca aaaccacaac agaaccccca   4800

atatcgcctc ttccttcact gcttgtcacg cctggtccgc cgaccgcagg ctttccccga   4860

gagccgcttc cccgagttca tgaacaacga cgcctccatc atccgctcct cccacgccga   4920

ctggctgctg gtggcggagc gcgacgccgc cacggccgcc gccgccaacg tgaacgccgc   4980

caccggcagc agcgccgccg cggccgccgc cgccgacgtg aacagcagct gccagtgcaa   5040

gggcatctac atggcggact cggcggccct ggtgggccgc tgcggcgcca cctcgcgccc   5100

cgcgctggcc gtggacgacg tgcacgtcgc cgagagtcac gcgcaggtct ggcgcggcct   5160

cgccggcctc cccccctcct cgtcgtccgc ctccaccgcc gccgcctctg cgtccgccgc   5220

ctcctctgcc gccagcggca ccgccagcac cctgggcagc tcggagggct actggctccg   5280

cgacctgggc agcggccgcg gcacctgggt caacggcaag cgcctgcccg acggcgccac   5340

ggtgcagctg tggcccggcg acgcggtgga gttcggccgg caccccagcc acgaggtgtt   5400

caaggtgaag atgcagcacg tgacgctgcg cagcgacgag ctcagcggcc aggcctacac   5460

cacgctcatg gtgggcaaga tccggaacaa cgactacgtc atgcccgagt cgcggccgga   5520
```

-continued cggcggcagc cagcagccgg gccgcctggt gacggcttaa gcggcgccgt gcgtaagggc 5580
cggcttacgg gggcggcagt gtcgctgtgg agggatggtc tggggtggga ggaatgggag 5640
gagagcggcg ggagcccgag gagcggagcg ctggaggctt gcggagcggc agcttgggaa 5700
gagctgcgga gagaggaagg agcgcagggc gcttggagca cgcgccagat tacgatcacg 5760
gcagcgcgag gcgcgcgtct gacttcgaag tggtaaggaa gatttcatgt atgattgcgt 5820
cgagggacac cgcaagtttt acgcgcggcg gagggagcct tggggcatac aacagtacga 5880
gcgggcgttg gtgagaaggt ggtcactccg tatgagaaga tggttactcc gtaccttcgt 5940
gagaagctgc tgcgcacaag ttacgaacct atctgtgtgg agagcccggt agtatatcag 6000
gggcgagggt catgaacgcg agtggcgagt ctgtgagcgc caatttgtta tgcggcataa 6060
tttcgcatcg ggtattacg tctacaaaat gttgagctgg cttagcgcag gaggcaacac 6120
ctcaggcaga atgtacgaat gtgtgcagaa gggcagagtc aaggcagagg cggagaagtt 6180
gtcagggctg tgtgtggttt ggtcagggcg tggctagatg gatatgagac ccgccgccgt 6240
ctccagattg tggcggaggt ggaactctcg gcccccgcgc cagtccccgc ggccagcgca 6300
tcccgccatg cgggttgttg gctggtgcat cgcgcggggt gtgctatgag tgtggaaaca 6360
ctatgtcgcg tgtcgtgctg aggtctgttg agaggtttcg tcgtttgtgc atgtcctgtc 6420
ccggttggag tttgagcgag gtggttcaaa gtttttggat cgcgtgggag agactgaaac 6480
ggtttggtga gaatggttga gacagaggtt gggcttggaa actggaggag aggagcagcg 6540
taactcgagg acgatgcagt agatgcacca caacagttgt ggtgggcgcc tggagtaaca 6600
cgcgtgccac caacacgcaa ttacagagat ccgtcataca ggagggatca tatgcgattt 6660
aattttggtt ttgcatttgt aagacgtttt caca 6694

<210> SEQ ID NO 7
<211> LENGTH: 23
<212> TYPE: DNA
<213> ORGANISM: Chlamydomonas reinhardtii

<400> SEQUENCE: 7
cccatccagg tgcgttcgcc gga 23

<210> SEQ ID NO 8
<211> LENGTH: 96
<212> TYPE: RNA
<213> ORGANISM: Artificial Sequence
<220> FEATURE:
<223> OTHER INFORMATION: gRNA

<400> SEQUENCE: 8
uccggcgaac gcaccuggau guuuuagagc uagaaauagc aaguuaaaau aaggcuaguc 60
cguuaucaac uugaaaaagu ggcaccgagu cggugc 96

<210> SEQ ID NO 9
<211> LENGTH: 1406
<212> TYPE: PRT
<213> ORGANISM: Chlamydomonas reinhardtii

<400> SEQUENCE: 9

Met Gly Ser Ser His His His His His His Val Tyr Pro Tyr Asp Val
1 5 10 15

Pro Asp Tyr Ala Glu Leu Pro Pro Lys Lys Lys Arg Lys Val Gly Ile
20 25 30

Arg Ile Pro Gly Glu Lys Pro Asp Lys Lys Tyr Ser Ile Gly Leu Asp

```
        35                  40                  45

Ile Gly Thr Asn Ser Val Gly Trp Ala Val Ile Thr Asp Glu Tyr Lys
    50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
    130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
        195                 200                 205

Glu Gly Asp Leu Asn Pro Asp Asn Ser Asp Val Asp Lys Leu Phe Ile
    210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
        275                 280                 285

Asn Phe Lys Ser Asn Phe Asp Leu Ala Glu Asp Ala Lys Leu Gln Leu
    290                 295                 300

Ser Lys Asp Thr Tyr Asp Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
        355                 360                 365

Asp Leu Thr Leu Leu Lys Ala Leu Val Arg Gln Gln Leu Pro Glu Lys
    370                 375                 380

Tyr Lys Glu Ile Phe Phe Asp Gln Ser Lys Asn Gly Tyr Ala Gly Tyr
385                 390                 395                 400

Ile Asp Gly Gly Ala Ser Gln Glu Glu Phe Tyr Lys Phe Ile Lys Pro
                405                 410                 415

Ile Leu Glu Lys Met Asp Gly Thr Glu Glu Leu Leu Val Lys Leu Asn
            420                 425                 430

Arg Glu Asp Leu Leu Arg Lys Gln Arg Thr Phe Asp Asn Gly Ser Ile
        435                 440                 445

Pro His Gln Ile His Leu Gly Glu Leu His Ala Ile Leu Arg Arg Gln
    450                 455                 460
```

-continued

```
Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
            500                 505                 510

Pro Trp Asn Phe Glu Glu Val Val Asp Lys Gly Ala Ser Ala Gln Ser
        515                 520                 525

Phe Ile Glu Arg Met Thr Asn Phe Asp Lys Asn Leu Pro Asn Glu Lys
    530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
            580                 585                 590

Thr Asn Arg Lys Val Thr Val Lys Gln Leu Lys Glu Asp Tyr Phe Lys
        595                 600                 605

Lys Ile Glu Cys Phe Asp Ser Val Glu Ile Ser Gly Val Glu Asp Arg
    610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
            660                 665                 670

Arg Leu Lys Thr Tyr Ala His Leu Phe Asp Asp Lys Val Met Lys Gln
        675                 680                 685

Leu Lys Arg Arg Arg Tyr Thr Gly Trp Gly Arg Leu Ser Arg Lys Leu
    690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
        755                 760                 765

Pro Ala Ile Lys Lys Gly Ile Leu Gln Thr Val Lys Val Val Asp Glu
    770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
            820                 825                 830

Ile Leu Lys Glu His Pro Val Glu Asn Thr Gln Leu Gln Asn Glu Lys
        835                 840                 845

Leu Tyr Leu Tyr Tyr Leu Gln Asn Gly Arg Asp Met Tyr Val Asp Gln
    850                 855                 860

Glu Leu Asp Ile Asn Arg Leu Ser Asp Tyr Asp Val Asp His Ile Val
865                 870                 875                 880
```

-continued

```
Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
            900                 905                 910

Val Val Lys Lys Met Lys Asn Tyr Trp Arg Gln Leu Leu Asn Ala Lys
        915                 920                 925

Leu Ile Thr Gln Arg Lys Phe Asp Asn Leu Thr Lys Ala Glu Arg Gly
    930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
            980                 985                 990

Val Ile Thr Leu Lys Ser Lys Leu  Val Ser Asp Phe Arg  Lys Asp Phe
        995                 1000                1005

Gln Phe  Tyr Lys Val Arg Glu  Ile Asn Asn Tyr His  His Ala His
    1010                 1015                 1020

Asp Ala  Tyr Leu Asn Ala Val  Val Gly Thr Ala Leu  Ile Lys Lys
    1025                 1030                 1035

Tyr Pro  Lys Leu Glu Ser Glu  Phe Val Tyr Gly Asp  Tyr Lys Val
    1040                 1045                 1050

Tyr Asp  Val Arg Lys Met Ile  Ala Lys Ser Glu Gln  Glu Ile Gly
    1055                 1060                 1065

Lys Ala  Thr Ala Lys Tyr Phe  Phe Tyr Ser Asn Ile  Met Asn Phe
    1070                 1075                 1080

Phe Lys  Thr Glu Ile Thr Leu  Ala Asn Gly Glu Ile  Arg Lys Arg
    1085                 1090                 1095

Pro Leu  Ile Glu Thr Asn Gly  Glu Thr Gly Glu Ile  Val Trp Asp
    1100                 1105                 1110

Lys Gly  Arg Asp Phe Ala Thr  Val Arg Lys Val Leu  Ser Met Pro
    1115                 1120                 1125

Gln Val  Asn Ile Val Lys Lys  Thr Glu Val Gln Thr  Gly Gly Phe
    1130                 1135                 1140

Ser Lys  Glu Ser Ile Leu Pro  Lys Arg Asn Ser Asp  Lys Leu Ile
    1145                 1150                 1155

Ala Arg  Lys Lys Asp Trp Asp  Pro Lys Lys Tyr Gly  Gly Phe Asp
    1160                 1165                 1170

Ser Pro  Thr Val Ala Tyr Ser  Val Leu Val Val Ala  Lys Val Glu
    1175                 1180                 1185

Lys Gly  Lys Ser Lys Lys Leu  Lys Ser Val Lys Glu  Leu Leu Gly
    1190                 1195                 1200

Ile Thr  Ile Met Glu Arg Ser  Ser Phe Glu Lys Asn  Pro Ile Asp
    1205                 1210                 1215

Phe Leu  Glu Ala Lys Gly Tyr  Lys Glu Val Lys Lys  Asp Leu Ile
    1220                 1225                 1230

Ile Lys  Leu Pro Lys Tyr Ser  Leu Phe Glu Leu Glu  Asn Gly Arg
    1235                 1240                 1245

Lys Arg  Met Leu Ala Ser Ala  Gly Glu Leu Gln Lys  Gly Asn Glu
    1250                 1255                 1260

Leu Ala  Leu Pro Ser Lys Tyr  Val Asn Phe Leu Tyr  Leu Ala Ser
    1265                 1270                 1275

His Tyr  Glu Lys Leu Lys Gly  Ser Pro Glu Asp Asn  Glu Gln Lys
```

```
    1280                1285                1290

Gln Leu  Phe Val Glu Gln His  Lys His Tyr Leu Asp  Glu Ile Ile
    1295                1300                1305

Glu Gln  Ile Ser Glu Phe Ser  Lys Arg Val Ile Leu  Ala Asp Ala
    1310                1315                1320

Asn Leu  Asp Lys Val Leu Ser  Ala Tyr Asn Lys His  Arg Asp Lys
    1325                1330                1335

Pro Ile  Arg Glu Gln Ala Glu  Asn Ile Ile His Leu  Phe Thr Leu
    1340                1345                1350

Thr Asn  Leu Gly Ala Pro Ala  Ala Phe Lys Tyr Phe  Asp Thr Thr
    1355                1360                1365

Ile Asp  Arg Lys Arg Tyr Thr  Ser Thr Lys Glu Val  Leu Asp Ala
    1370                1375                1380

Thr Leu  Ile His Gln Ser Ile  Thr Gly Leu Tyr Glu  Thr Arg Ile
    1385                1390                1395

Asp Leu  Ser Gln Leu Gly Gly  Asp
    1400                1405


<210> SEQ ID NO 10
<211> LENGTH: 76
<212> TYPE: DNA
<213> ORGANISM: Artificial Sequence
<220> FEATURE:
<223> OTHER INFORMATION: Synthetic sequence

<400> SEQUENCE: 10

gttttagagc tagaaatagc aagttaaaat aaggctagtc cgttatcaac ttgaaaaagt     60

ggcaccgagt cggtgc                                                     76


<210> SEQ ID NO 11
<211> LENGTH: 23
<212> TYPE: DNA
<213> ORGANISM: Artificial Sequence
<220> FEATURE:
<223> OTHER INFORMATION: Synthetic sequence

<400> SEQUENCE: 11

tccggcgaac gcacctggat ggg                                             23


<210> SEQ ID NO 12
<211> LENGTH: 23
<212> TYPE: DNA
<213> ORGANISM: Artificial Sequence
<220> FEATURE:
<223> OTHER INFORMATION: Synthetic sequence

<400> SEQUENCE: 12

caccagctgc gcgaccgagc tgg                                             23


<210> SEQ ID NO 13
<211> LENGTH: 23
<212> TYPE: DNA
<213> ORGANISM: Artificial Sequence
<220> FEATURE:
<223> OTHER INFORMATION: Synthetic sequence

<400> SEQUENCE: 13

gccgttgcac ttctgaagca ggg                                             23


<210> SEQ ID NO 14
<211> LENGTH: 23
```

<212> TYPE: DNA
<213> ORGANISM: Artificial Sequence
<220> FEATURE:
<223> OTHER INFORMATION: Synthetic sequence

<400> SEQUENCE: 14
tccggcgaac gcacctggat ggg 23

<210> SEQ ID NO 15
<211> LENGTH: 23
<212> TYPE: DNA
<213> ORGANISM: Artificial Sequence
<220> FEATURE:
<223> OTHER INFORMATION: Synthetic sequence

<400> SEQUENCE: 15
tggtgggcgc cgacggcatc tgg 23

<210> SEQ ID NO 16
<211> LENGTH: 23
<212> TYPE: DNA
<213> ORGANISM: Artificial Sequence
<220> FEATURE:
<223> OTHER INFORMATION: Synthetic sequence

<400> SEQUENCE: 16
ccatggcttc gcaggcatct cgg 23

<210> SEQ ID NO 17
<211> LENGTH: 83
<212> TYPE: DNA
<213> ORGANISM: Artificial Sequence
<220> FEATURE:
<223> OTHER INFORMATION: Synthetic sequence

<400> SEQUENCE: 17
gccatccgcg gcgagggcaa gtaccgtgga cccatccagg tgcgttcgcc ggaacaccaa 60
cgcgcttgtt tttgctgtgc cgc 83

<210> SEQ ID NO 18
<211> LENGTH: 85
<212> TYPE: DNA
<213> ORGANISM: Artificial Sequence
<220> FEATURE:
<223> OTHER INFORMATION: Synthetic sequence

<400> SEQUENCE: 18
gccatccgcg gcgagggcaa gtaccgtgga cccatctcca ggtgcgttcg ccggaacacc 60
aacgcgcttg tttttgctgt gccgc 85

<210> SEQ ID NO 19
<211> LENGTH: 82
<212> TYPE: DNA
<213> ORGANISM: Artificial Sequence
<220> FEATURE:
<223> OTHER INFORMATION: Synthetic sequence

<400> SEQUENCE: 19
gccatccgcg gcgagggcaa gtaccgtgga cccatcaggt gcgttcgccg gaacaccaac 60
gcgcttgttt ttgctgtgcc gc 82

<210> SEQ ID NO 20
<211> LENGTH: 79
<212> TYPE: DNA

<213> ORGANISM: Artificial Sequence
<220> FEATURE:
<223> OTHER INFORMATION: Synthetic sequence

<400> SEQUENCE: 20
gccatccgcg gcgagggcaa gtaccgtgga cccaggtgcg ttcgccggaa caccaacgcg 60
cttgtttttg ctgtgccgc 79

<210> SEQ ID NO 21
<211> LENGTH: 89
<212> TYPE: DNA
<213> ORGANISM: Artificial Sequence
<220> FEATURE:
<223> OTHER INFORMATION: Synthetic sequence

<400> SEQUENCE: 21
gccatccgcg gcgagggcaa gtaccgtgga cccatcaaca tccaggtgcg ttcgccggaa 60
caccaacgcg cttgtttttg ctgtgccgc 89

<210> SEQ ID NO 22
<211> LENGTH: 84
<212> TYPE: DNA
<213> ORGANISM: Artificial Sequence
<220> FEATURE:
<223> OTHER INFORMATION: Synthetic sequence

<400> SEQUENCE: 22
gccatccgcg gcgagggcaa gtaccgtgga cccatctcag gtgcgttcgc cggaacacca 60
acgcgcttgt ttttgctgtg ccgc 84

<210> SEQ ID NO 23
<211> LENGTH: 12
<212> TYPE: DNA
<213> ORGANISM: Chlamydomonas reinhardtii

<400> SEQUENCE: 23
cccatccagg tg 12

<210> SEQ ID NO 24
<211> LENGTH: 54
<212> TYPE: DNA
<213> ORGANISM: Artificial Sequence
<220> FEATURE:
<223> OTHER INFORMATION: Synthetic sequence

<400> SEQUENCE: 24
cccatcgaaa ttaataagac tcattatatt ccggcgaacg cacctggaca ggtg 54

<210> SEQ ID NO 25
<211> LENGTH: 56
<212> TYPE: DNA
<213> ORGANISM: Artificial Sequence
<220> FEATURE:
<223> OTHER INFORMATION: Synthetic sequence

<400> SEQUENCE: 25
cccatctagc tctaaaacat ccaggtgcgt tcgccggact atagtgagta caggtg 56

<210> SEQ ID NO 26
<211> LENGTH: 13
<212> TYPE: DNA
<213> ORGANISM: Artificial Sequence -continued

```
<220> FEATURE:
<223> OTHER INFORMATION: Synthetic sequence

<400> SEQUENCE: 26

cccatcacag gtg                                                    13
```